(12) United States Patent
Ajima

(10) Patent No.: US 11,464,431 B2
(45) Date of Patent: Oct. 11, 2022

(54) ELECTRONIC DEVICE, ESTIMATION SYSTEM, ESTIMATION METHOD, AND ESTIMATION PROGRAM

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 16/970,250

(22) PCT Filed: Feb. 1, 2019

(86) PCT No.: PCT/JP2019/003709
§ 371 (c)(1),
(2) Date: Aug. 14, 2020

(87) PCT Pub. No.: WO2019/176362
PCT Pub. Date: Sep. 19, 2019

(65) Prior Publication Data
US 2021/0137425 A1  May 13, 2021

(30) Foreign Application Priority Data
Mar. 12, 2018 (JP) .............................. JP2018-044750

(51) Int. Cl.
*A61B 5/145* (2006.01)
*A61B 5/021* (2006.01)
*A61B 5/00* (2006.01)

(52) U.S. Cl.
CPC ...... *A61B 5/14532* (2013.01); *A61B 5/02108* (2013.01); *A61B 5/14546* (2013.01); *A61B 5/7235* (2013.01)

(58) Field of Classification Search
CPC . A61B 5/14532; A61B 5/021; A61B 5/02108; A61B 5/02125; A61B 5/14546; A61B 5/72; A61B 5/7264–7267; A61B 5/02; A61B 5/02007; A61B 5/02035; A61B 5/0205; A61B 5/024; A61B 5/02416;
(Continued)

(56) References Cited

U.S. PATENT DOCUMENTS

2006/0224070 A1* 10/2006 Sharrock ............ A61B 5/02007
600/500
2015/0031964 A1* 1/2015 Bly ........................ A61B 5/681
600/301
(Continued)

FOREIGN PATENT DOCUMENTS

JP  2002-360530 A  12/2002
WO  2016174839 A1  11/2016

OTHER PUBLICATIONS

Machine Translation of WO 2016/174839 (Year: 2021).*
(Continued)

*Primary Examiner* — Eric F Winakur
*Assistant Examiner* — Alice Ling Zou
(74) *Attorney, Agent, or Firm* — Studebaker & Brackett PC

(57) ABSTRACT

An electronic device includes a sensor configured to acquire a pulse wave of a subject and a controller configured to analyze, based on the pulse wave of the subject acquired by the sensor, the rate of change in the pulse wave at a predetermined time after the point in time exhibiting a peak of the pulse wave and to estimate the blood glucose level of the subject based on the rate of change.

15 Claims, 25 Drawing Sheets

(58) Field of Classification Search
CPC . A61B 5/02438; A61B 5/0244; A61B 5/0255; A61B 5/02116; A61B 5/681; A61B 5/7235
See application file for complete search history.

(56) References Cited

U.S. PATENT DOCUMENTS

2018/0116571 A1    5/2018  Ajima
2019/0110751 A1*   4/2019  Lee ..................... A61B 5/7221

OTHER PUBLICATIONS

Westerhof, Berend E.; van den Winjngaard, Jeroen P.; Murgo, Joseph P.; Westerhof, Nicolaas. "Location of a Reflection Site is Elusive," Hypertension, vol. 52, No. 3, 478-483 (Year: 2008).*

* cited by examiner

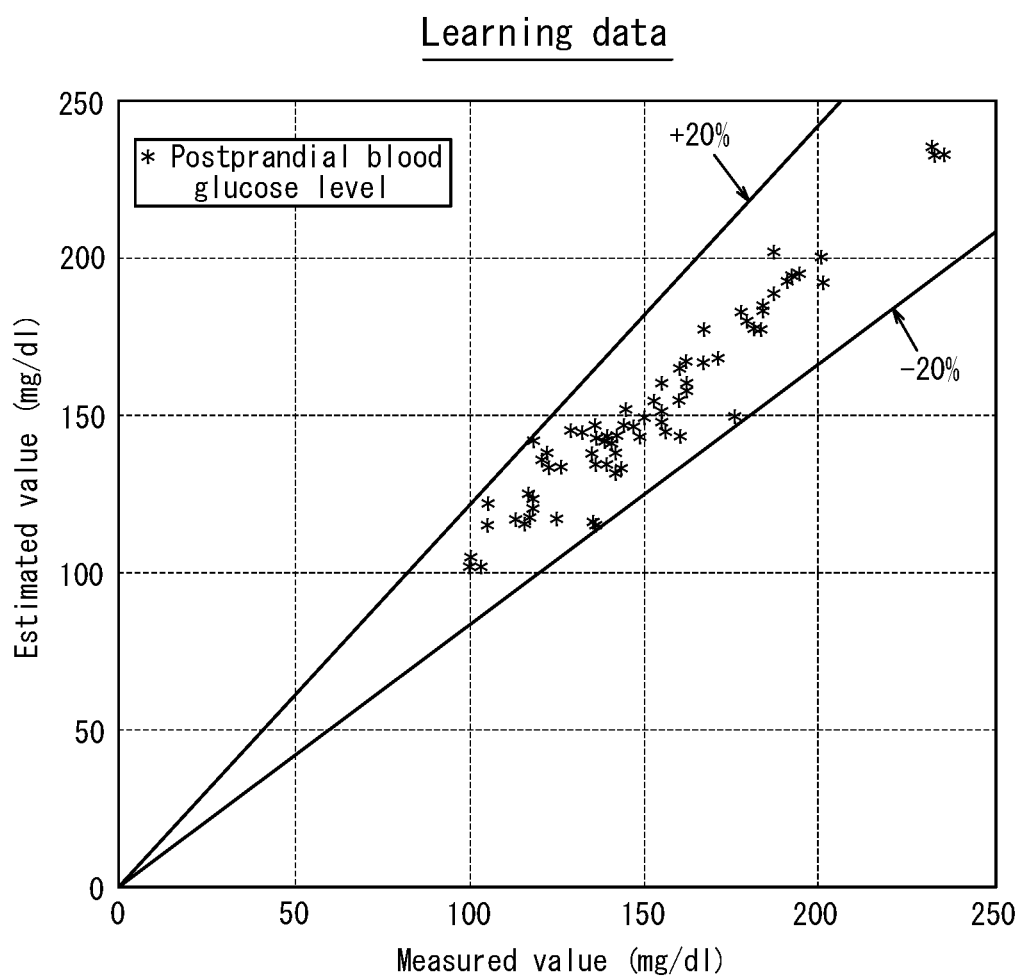

ELECTRONIC DEVICE, ESTIMATION SYSTEM, ESTIMATION METHOD, AND ESTIMATION PROGRAM

CROSS-REFERENCE TO RELATED APPLICATION

The present application claims priority to and the benefit of Japanese Patent Application No. 2018-044750 filed Mar. 12, 2018, the entire contents of which are incorporated herein by reference.

TECHNICAL FIELD

The present disclosure relates to an electronic device, an estimation system, an estimation method, and an estimation program that estimate a subject's state of health from measured biological information.

BACKGROUND

Conventionally, a subject's (user's) state of health has been estimated by measuring a blood component or measuring the blood fluidity. These measurements are made using a blood sample collected from the subject. An electronic device that measures biological information from the wrist or other measured part of a subject is also known. For example, an electronic device measures a subject's pulse rate by being attached to the subject's wrist.

SUMMARY

An electronic device according to an embodiment includes a sensor configured to acquire a pulse wave of a subject, and a controller configured to analyze, based on the pulse wave of the subject acquired by the sensor, a rate of change in the pulse wave at a predetermined time after a point in time exhibiting a peak of the pulse wave and to estimate a blood glucose level of the subject based on the rate of change.

An electronic device according to another embodiment includes a sensor configured to acquire a pulse wave of a subject, and a controller configured to analyze, based on the pulse wave of the subject acquired by the sensor, a rate of change in the pulse wave at a predetermined time after a point in time exhibiting a peak of the pulse wave and to estimate a lipid level of the subject based on the rate of change.

An estimation system according to an embodiment includes an electronic device and an information processing apparatus connected communicably with each other. The electronic device includes a sensor configured to acquire a pulse wave of a subject. The information processing apparatus includes a controller configured to analyze, based on the pulse wave of the subject acquired by the sensor, a rate of change in the pulse wave at a predetermined time after a point in time exhibiting a peak of the pulse wave and to estimate a blood glucose level of the subject based on the rate of change.

An estimation system according to an embodiment includes an electronic device and an information processing apparatus connected communicably with each other. The electronic device includes a sensor configured to acquire a pulse wave of a subject. The information processing apparatus includes a controller configured to analyze, based on the pulse wave of the subject acquired by the sensor, a rate of change in the pulse wave at a predetermined time after a point in time exhibiting a peak of the pulse wave and to estimate a lipid level of the subject based on the rate of change.

An estimation method according to an embodiment is an estimation method to be executed by an electronic device. The estimation method includes acquiring a pulse wave of a subject; analyzing, based on the pulse wave of the subject, a rate of change in the pulse wave at a predetermined time after a point in time exhibiting a peak of the pulse wave; and estimating a blood glucose level of the subject based on the rate of change.

An estimation method according to an embodiment is an estimation method to be executed by an electronic device. The estimation method includes acquiring a pulse wave of a subject; analyzing, based on the pulse wave of the subject, a rate of change in the pulse wave at a predetermined time after a point in time exhibiting a peak of the pulse wave; and estimating a lipid level of the subject based on the rate of change.

An estimation program according to an embodiment is for causing an electronic device to execute the steps of acquiring a pulse wave of a subject; analyzing, based on the pulse wave of the subject, a rate of change in the pulse wave at a predetermined time after a point in time exhibiting a peak of the pulse wave; and estimating a blood glucose level of the subject based on the rate of change.

An estimation program according to an embodiment is for causing an electronic device to execute the steps of acquiring a pulse wave of a subject; analyzing, based on the pulse wave of the subject, a rate of change in the pulse wave at a predetermined time after a point in time exhibiting a peak of the pulse wave; and estimating a lipid level of the subject based on the rate of change.

BRIEF DESCRIPTION OF THE DRAWINGS

In the accompanying drawings:

FIG. 21A is a graph illustrating learning data for neural network regression analysis;

DETAILED DESCRIPTION

The pain involved in collecting a blood sample prevents subjects from estimating their own state of health routinely. Furthermore, an electronic device that only measures pulse is unable to measure the subject's state of health apart from the pulse. The present disclosure therefore provides an electronic device, an estimation system, an estimation method, and an estimation program that can easily estimate a subject's state of health.

Embodiments are described below in detail with reference to the drawings.

First Embodiment

Figure 1:
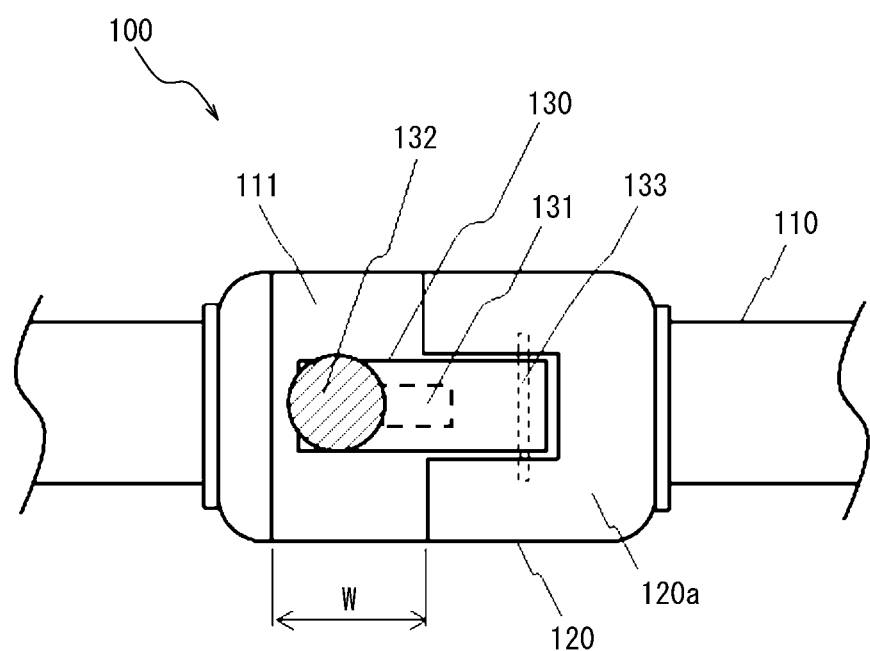
FIG. 1 illustrates the schematic configuration of an example of an electronic device according to an embodiment.

FIG. 1 illustrates the schematic configuration of a first example of an electronic device according to an embodiment. An electronic device 100 of the first example illustrated in FIG. 1 includes a wearing portion 110 and a measurement unit 120. FIG. 1 is a view of the electronic device 100 of the first example from a back face 120a that conies into contact with the measured part.

The electronic device 100 measures the subject's biological information while the electronic device 100 is worn by the subject. The biological information measured by the electronic device 100 includes the subject's pulse wave. In an embodiment, the electronic device 100 of the first example may acquire the pulse wave while being worn on the subject's wrist.

In an embodiment, the wearing portion 110 is a straight, elongated hand. The pulse wave is, for example, measured in a state in which the subject has wrapped the wearing portion 110 of the electronic device 100 around the wrist. In greater detail, the subject wraps the wearing portion 110 around the wrist so that the back face 120a of the measurement unit 120 is in contact with the measured part and then measures the pulse wave. The electronic device 100 measures the pulse wave of blood flowing through the ulnar artery or the radial artery of the subject.

Figure 2:
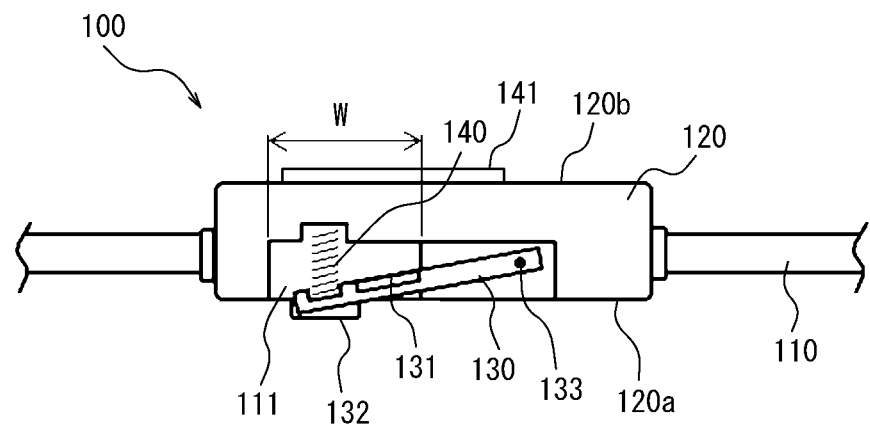
FIG. 2 is a cross-section schematically illustrating the configuration of the electronic device of FIG. 1.

FIG. 2 is a cross-section of the electronic device 100 of the first example. FIG. 2 illustrates the measurement unit 120 and the wearing portion 110 around the measurement unit 120.

The measurement unit 120 includes the back face 120a in contact with the subject's wrist while worn and a front face 120b opposite the back face 120a. The measurement unit 120 includes an opening 111 on the back face 120a side. A sensor 130 includes a first end that touches the subject's wrist when the electronic device 100 of the first example is worn and a second end in contact with the measurement unit 120. In a state in which an elastic body 140 is not pressed, the first end of the sensor 130 protrudes from the opening 111 at the back face 120a. The first end of the sensor 130 includes a pulse pad 132. The first end of the sensor 130 is displaceable in a direction substantially perpendicular to the plane of the back face 120a. The second end of the sensor 130 is in contact with the measurement unit 120 via a shaft 133.

The first end of the sensor 130 is in contact with the measurement unit 120 via the elastic body 140. The first end of the sensor 130 is displaceable relative to the measurement unit 120. The elastic body 140 includes a spring, for example. The elastic body 140 is not limited to being a spring and can be any other elastic body, such as resin or a sponge. Instead of or along with the elastic body 140, a biasing mechanism such as a torsion coil spring may be provided on the rotation shaft 133 of the sensor 130, and the pulse pad 132 of the sensor 130 may be placed in contact with the measured part that is subjected to measurement of the pulse wave of the subject's blood.

A controller, storage, communication interface, power source, notification interface, circuits for causing these components to operate, cables for connecting these components, and the like may be disposed in the measurement unit 120.

The sensor 130 includes an angular velocity sensor 131 that detects displacement of the sensor 130. The angular velocity sensor 131 detects the angular displacement of the sensor 130. The type of sensor provided in the sensor 130 is not limited to the angular velocity sensor 131 and may, for example, be an acceleration sensor, an angle sensor, another motion sensor, or a plurality of these sensors.

The electronic device 100 of the first example includes an input interface 141 on the front face 120b of the measurement unit 120. The input interface 141 receives operation input from the subject and may be configured, for example, using operation buttons (operation keys). The input interface 141 may, for example, be configured by a touchscreen.

Figure 3:
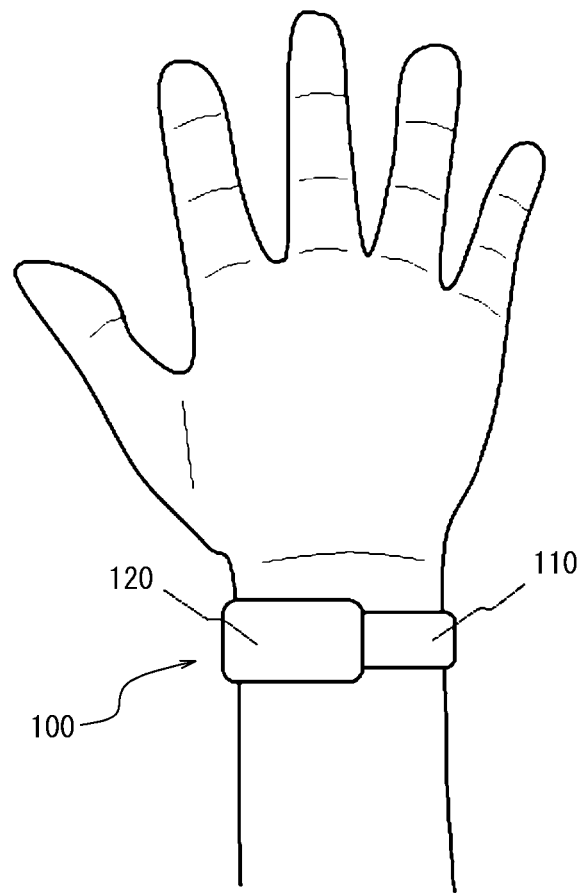
FIG. 3 illustrates an example of a usage state of the electronic device in FIG. 1.

FIG. 3 illustrates an example of a usage state of the electronic device 100 of the first example by the subject. The subject wraps the electronic device 100 of the first example around the wrist for use. The electronic device 100 of the first example is worn in a state such that the back face 120a of the measurement unit 120 is in contact with the wrist.

With the electronic device 100 of the first example wrapped around the wrist, the position of the measurement unit 120 can be adjusted so that the pulse pad 132 is in contact with the position of the ulnar artery or the radial artery.

In FIG. 3, while the electronic device 100 of the first example is worn, the first end of the sensor 130 is in contact with the skin above the radial artery, which is the artery on the thumb side of the subject's left hand. The first end of the sensor 130 is in contact with the skin above the subject's radial artery as a result of the elastic force of the elastic body 140 arranged between the measurement unit 120 and the sensor 130. The sensor 130 is displaced in accordance with the movement of the subject's radial artery, i.e. pulsation. The angular velocity sensor 131 detects displacement of the sensor 130 and acquires the pulse wave. The pulse wave refers to a waveform representation of the temporal change, acquired from the body surface, in volume of a blood vessel due to inflow of blood.

Referring again to FIG. 2, in a state in which an elastic body 140 is not pressed, the first end of the sensor 130 protrudes from the opening 111. When the electronic device 100 of the first example is worn by the subject, the first end of the sensor 130 is in contact with the skin above the subject's radial artery, and in accordance with pulsation, the elastic body 140 expands and contracts, displacing the first end of the sensor 130. A component with an appropriate elastic modulus is used for the elastic body 140 so as to expand and contract in accordance with pulsation without inhibiting pulsation. The opening width W of the opening 111 is greater than the vessel diameter, i.e. the radial artery diameter in an embodiment. By the opening 111 being provided in the measurement unit 120, the back face 120a of the measurement unit 120 does not compress the radial artery when the electronic device 100 of the first example is worn. Therefore, the electronic device 100 of the first example can acquire a pulse wave with little noise, improving measurement accuracy.

FIG. 3 illustrates an example in which the electronic device 100 of the first example is worn on the wrist and acquires the pulse wave at the radial artery, but the electronic device 100 of the first example may, for example, acquire the pulse wave of blood flowing through a carotid artery at the subject's neck. In greater detail, the subject may press the pulse pad 132 lightly against the position of the carotid artery to measure the pulse wave. The subject may also wrap the electronic device 100 of the first example around the neck so that the pulse pad 132 is at the position of the carotid artery.

Figure 4:
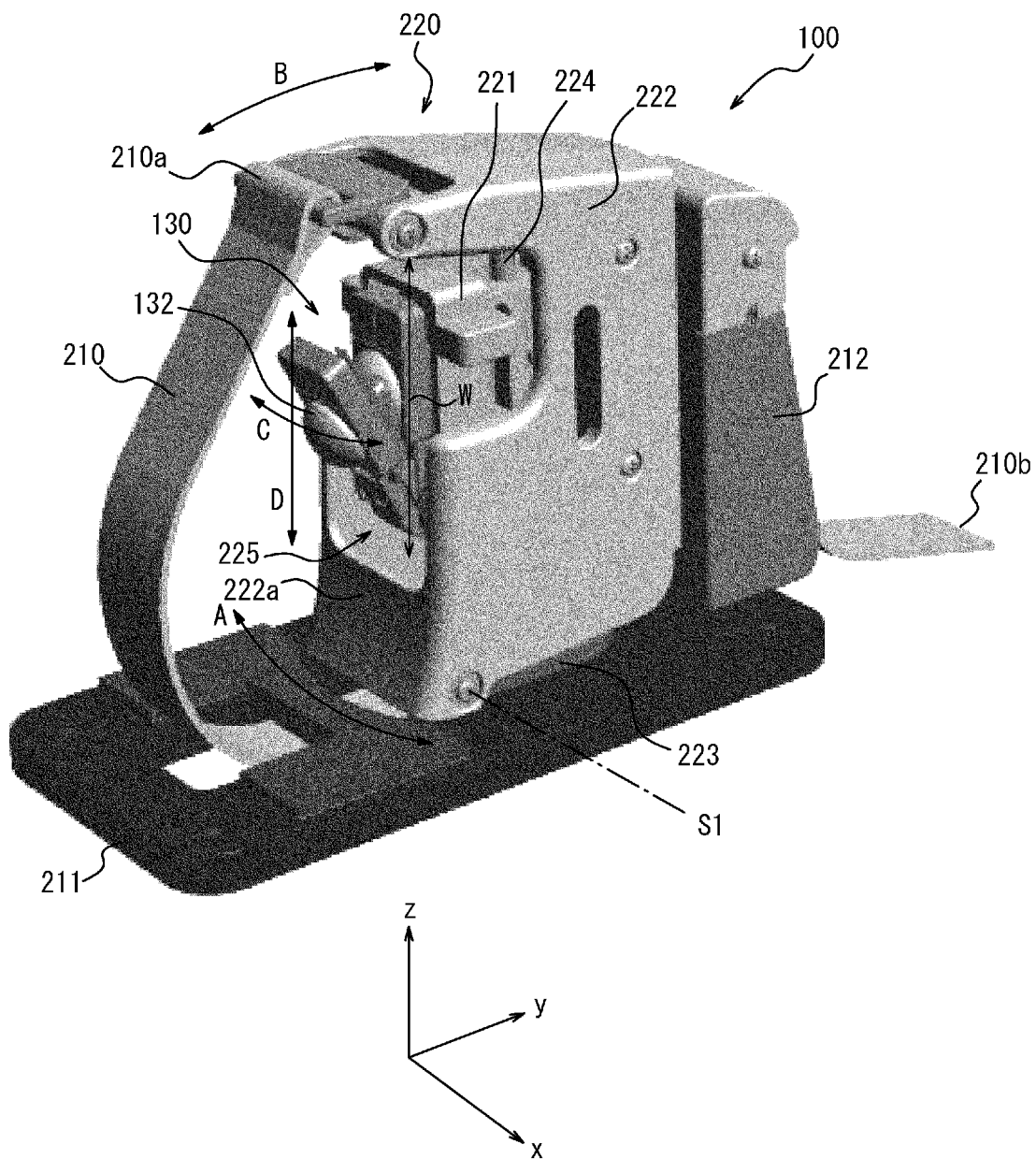
FIG. 4 is an external perspective view schematically illustrating an example of an electronic device according to an embodiment.

FIG. 4 is an external perspective view schematically illustrating a second example of an electronic device according to an embodiment. An electronic device 100 of the second example illustrated in FIG. 4 includes a wearing portion 210, a base 211, and a fixing portion 212 and measurement unit 220 attached to the base 211.

In the present embodiment, the base 211 is a substantially rectangular flat plate. In the present disclosure, the direction of the short sides of the flat plate-shaped base 211 is considered the x-axis direction, the direction of the long sides of the flat plate-shaped base 211 is considered the y-axis direction, and the orthogonal direction of the flat plate-shaped base 211 is considered the z-axis direction, as illustrated in FIG. 4. A portion of the electronic device 100 of the second example is configured to be moveable, as described in the present disclosure. When describing the direction with regard to the electronic device 100 of the second example in the present disclosure, the x, y, and z-axis directions in the state in FIG. 4 are implied, unless otherwise noted. In the present disclosure, the positive z-axis direction is referred to as up, the negative z-axis direction as down, and the positive x-axis direction as the front of the electronic device 100 of the second example.

The electronic device 100 of the second example measures the subject's biological information while the subject wears the electronic device 100 of the second example using the wearing portion 210. The biological information measured by the electronic device 100 of the second example is the subject's pulse wave, which is measurable by the measurement unit 220. As one example, the electronic device 100 of the second example is described below as being worn on the subject's wrist and acquiring a pulse wave.

Figure 5:
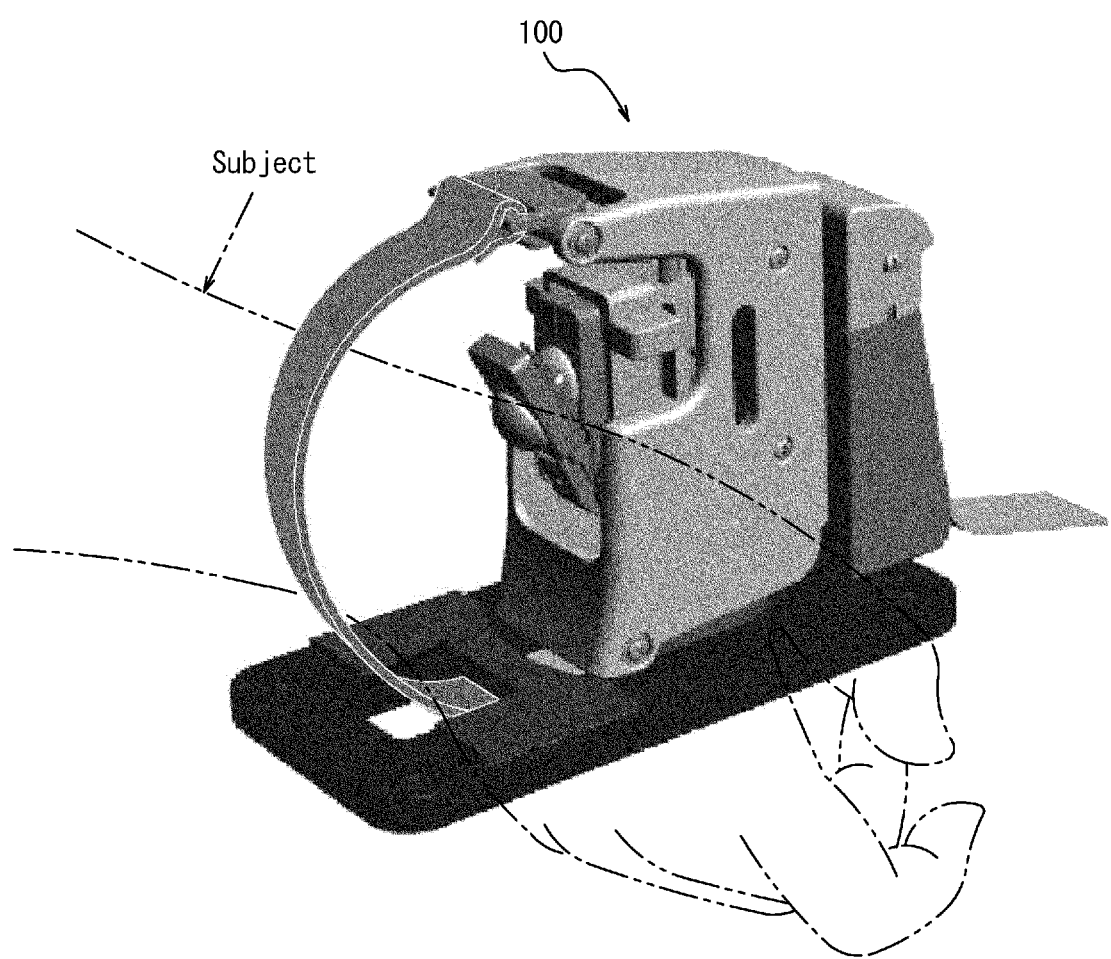
FIG. 5 schematically illustrates a state in which the electronic device of FIG. 4 is worn.

FIG. 5 schematically illustrates a state in which a subject is wearing the electronic device 100 of the second example in FIG. 4. The subject can wear the electronic device 100 as illustrated in FIG. 5 by inserting a wrist into the space formed by the wearing portion 210, the base 211, and the measurement unit 220 and fixing the wrist in place with the wearing portion 210. In the example illustrated in FIGS. 4 and 5, the subject wears the electronic device 100 of the second example by inserting the wrist along the x-axis in the positive x-axis direction through the space formed by the wearing portion 210, the base 211, and the measurement unit 220. The subject wears the electronic device 100 of the second example so that, for example, the pulse pad 132 of the measurement unit 220, described below, is in contact with the position of the ulnar artery or the radial artery. The electronic device 100 of the second example measures the pulse wave of blood flowing through the ulnar artery or the radial artery at the subject's wrist.

The measurement unit 220 includes a body 221, an exterior portion 222, and a sensor 130. The sensor 130 is attached to the body 221. The measurement unit 220 is attached to the base 211 via a connecting portion 223.

The connecting portion 223 may be attached to the base 211 in a rotatable manner along the surface of the base 211. In other words, in the example in FIG. 4, the connecting portion 223 may be attached to the base 211 in a rotatable manner in the xy plane relative to the base 211, as indicated by the arrow A. In this case, the entire measurement unit 220 attached to the base 211 via the connecting portion 223 is rotatable in the xy plane relative to the base 211.

The exterior portion 222 is connected to the connecting portion 223 along a shaft S1 that passes through the connecting portion 223. The shaft S1 is a shaft extending in the x-axis direction. By the exterior portion 222 being connected to the connecting portion 223 in this way, the exterior portion 222 is displaceable relative to the connecting portion 223 along a plane intersecting the xy plane along which the base 211 extends. In other words, the exterior portion 222 can be inclined about the shaft S1 at a predetermined angle to the xy plane along which the base 211 extends. The exterior portion 222 can, for example, be displaced while positioned on a plane having a predetermined inclination relative to the xy plane, such as the yz plane. In the present embodiment, the exterior portion 222 can be connected to the connecting portion 223 in a rotatable manner, in the yz plane orthogonal to the xy plane, about the shaft S1 as indicated by the arrow B in FIG. 4.

The exterior portion 222 includes a contact surface 222a that comes in contact with the subject's wrist when the electronic device 100 of the second example is worn. The exterior portion 222 may include an opening 225 on the contact surface 222a side. The exterior portion 222 may be configured to cover the body 221.

The exterior portion 222 may include a shaft 224, extending in the z-axis direction, in an interior space. The body 221 includes a hole through which the shaft 224 is passed. The body 221 is attached in the interior space of the exterior portion 222 with the shaft 224 passed through the hole. In other words, the body 221 is attached to the exterior portion 222 in a rotatable manner, in the xy plane, about the shaft 224 relative to the exterior portion 222, as indicated by the arrow C in FIG. 4. The body 221 is thus attached to the exterior portion 222 in a rotatable manner along the xy plane, which is the surface of the base 211, relative to the exterior portion 222. The body 221 is also attached to the exterior portion 222 in a displaceable manner in the up-down direction relative to the exterior portion 222, along the shaft 224, i.e. along the z-axis direction, as indicated by the arrow D in FIG. 4.

Figure 6:
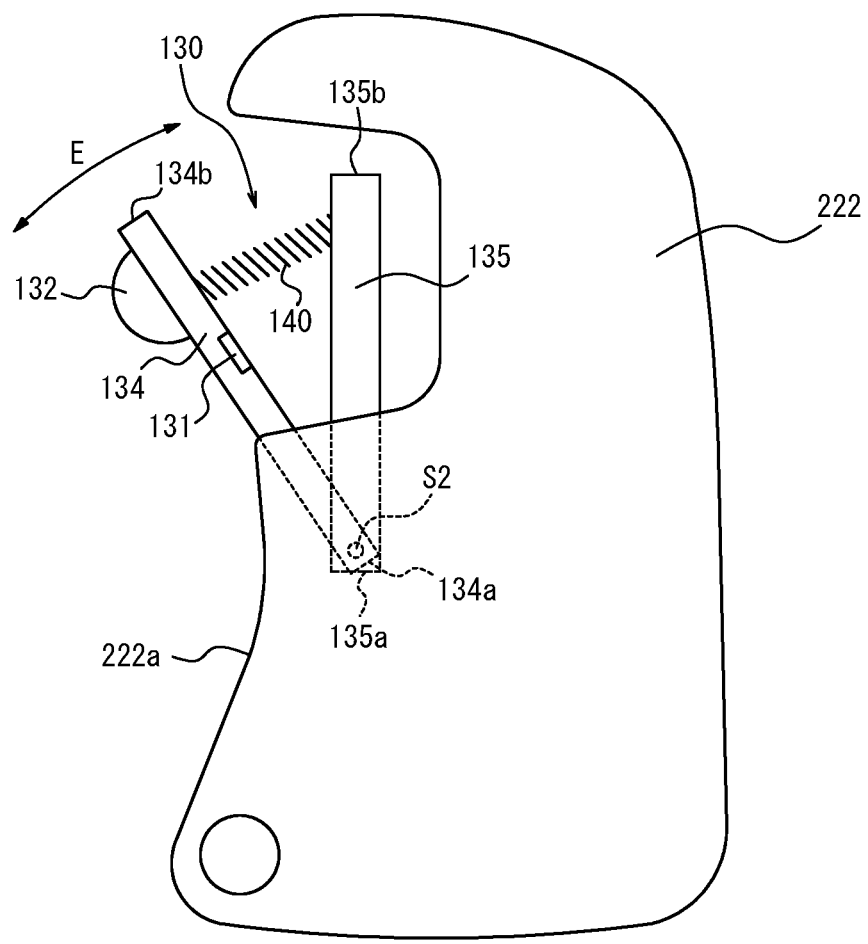
FIG. 6 schematically illustrates an exterior portion and a sensor in a front view of the electronic device of FIG. 4.

The sensor 130 is attached to the body 221. Details of the sensor 130 are described with reference to FIG. 6, which schematically illustrates the exterior portion 222 and the sensor 130 in a front view of the electronic device 100 of the second example. In FIG. 6, the portions of the sensor 130 that overlap with the exterior portion 222 in the front view are indicated by dashed lines.

The sensor 130 includes a first arm 134 and a second arm 135. The second arm 135 is fixed to the body 221. An end 135a of the second arm 135 at the lower side is connected to an end 134a of the first arm 134. The first arm 134 is connected to the second arm 135 so that the other end 134b is rotatable in the yz plane with the end 134a as the axis of rotation, as indicated by the arrow E in FIG. 6.

The other end 134b of the first arm 134 is connected to the other end 135b of the second arm 135 at the upper side via the elastic body 140. The first arm 134 is supported by the second arm 135 in a state such that the first arm 134 is not being pressed by the elastic body 140, and the other side 134b of the sensor 130 is protruding from the opening 225 of the exterior portion 222 towards the contact surface 222a side. The elastic body 140 is, for example, a spring. The elastic body 140 is not limited to being a spring, however, and can be any other elastic body, such as resin or a sponge. Instead of or along with the elastic body 140, a biasing mechanism such as a torsion coil spring may be provided on a rotation shaft S2 of the first arm 134, and the pulse pad 132 of the first arm 134 may be placed in contact with the measured part that is subjected to measurement of the pulse wave of the subject's blood.

The pulse pad 132 is connected to the other end 134b of the first arm 134. The pulse pad 132 is the portion placed in contact with the measured part targeted for measurement of the pulse wave of the subject's blood when the electronic device 100 of the second example is worn. In the present embodiment, the pulse pad 132 is, for example, in contact with the position of the ulnar artery or the radial artery. The pulse pad 132 may be configured by a material that does not easily absorb changes in body surface due to the subject's pulse. The pulse pad 132 may be configured by a material that is not painful for the user in a state of contact. For example, the pulse pad 132 may be formed by a cloth bag filled with beads. The pulse pad 132 may, for example, be configured to be detachable from the first arm 134. The subject may, for example, attach one pulse pad 132 to the first arm 134 from among a plurality of sizes and/or shapes of pulse pads 132 in accordance with the size and/or shape of the subject's wrist. This enables the subject to use the pulse pad 132 in accordance with the size and/or shape of the subject's wrist.

The sensor 130 includes an angular velocity sensor 131 that detects displacement of the first arm 134. It suffices for the angular velocity sensor 131 to be capable of detecting the angular displacement of the first arm 134. The type of sensor provided in the sensor 130 is not limited to the angular velocity sensor 131 and may, for example, be an acceleration sensor, an angle sensor, another motion sensor, or a plurality of these sensors.

While the electronic device 100 of the second example is worn in the present embodiment, the pulse pad 132 is in contact with the skin above the radial artery, which is the artery on the thumb side of the subject's right hand, as illustrated in FIG. 5. The elastic force of the elastic body 140 disposed between the second arm 135 and the first arm 134 places the pulse pad 132 disposed at the other end 134b of the first arm 134 in contact with the skin above the radial artery of the subject. The first arm 134 is displaced in accordance with the movement of the subject's radial artery, i.e. pulsation. The angular velocity sensor 131 acquires the pulse wave by detecting displacement of the first arm 134. The pulse wave refers to a waveform representation of the temporal change in volume of a blood vessel due to inflow of blood, acquired from the body surface.

As illustrated in FIG. 6, the other end 134b of the first arm 134 protrudes from the opening 225 while the elastic body 140 is not being pressed. When the subject wears the electronic device 100, the pulse pad 132 connected to the first arm 134 comes into contact with the skin above the radial artery of the subject. The elastic body 140 expands and contracts in accordance with pulsation, and the pulse pad 132 is displaced. A component with an appropriate elastic modulus is used for the elastic body 140 so as to expand and contract in accordance with pulsation without inhibiting pulsation. The opening width W of the opening 225 is sufficiently greater than the vessel diameter, i.e. the radial artery diameter in the present embodiment. By the opening 225 being provided in the exterior portion 222, the contact surface 222a of the exterior portion 222 does not compress the radial artery when the electronic device 100 of the second example is worn. Therefore, the electronic device 100 of the second example can acquire a pulse wave with little noise, improving measurement accuracy.

The fixing portion 212 is fixed to the base 211. The fixing portion 212 may include a fixing mechanism for fixing the wearing portion 210. Each functional component used for the electronic device 100 of the second example to measure the pulse wave may be included inside the wearing portion 210. For example, the fixing portion 212 may include the below-described input interface, controller, power source, storage, communication interface, notification interface, circuits for causing these components to operate, cables for connecting these components, and the like.

The wearing portion 210 is a mechanism used for fixing the subject's wrist to the electronic device 100 of the second example. In the example illustrated in FIG. 4, the wearing portion 210 is a straight, elongated band. The wearing portion 210 in the example illustrated in FIG. 4 is arranged so that one end 210a is connected to the upper end of the measurement unit 220, the wearing portion 210 passes through the inside of the base 211, and another end 210b is located in the positive direction of the y-axis. For example, the subject inserts his right wrist into the space formed by the wearing portion 210, the base 211, and the measurement unit 220 and pulls the other end 210b of the wearing portion 210 in the positive direction of the y-axis with the left hand while making adjustments so that the pulse pad 132 comes into contact with the skin above the radial artery of the right wrist. The subject pulls the other end 210b enough for the right wrist to be fixed to the electronic device 100 of the second example and fixes the wearing portion 210 in this state with the fixing mechanism of the fixing portion 212. In this way, the subject can put on the electronic device 100 of the second example with one hand (the left hand in the present embodiment). The subject can also use the wearing portion 210 to fix the wrist to the electronic device 100 of the second example, thereby stabilizing the wearing state of the electronic device 100 of the second example. Consequently, the positional relationship between the wrist and the electronic device 100 of the second example is less likely to change during measurement. This enables stable measurement of the pulse wave and improves measurement accuracy.

Next, movement of the moveable portion of the electronic device 100 of the second example at the time of wearing of the electronic device 100 of the second example is described.

To wear the electronic device 100 of the second example, the subject inserts the wrist along the x-axis direction into the space formed by the wearing portion 210, the base 211, and the measurement unit 220, as described above. The measurement unit 220 is configured to be rotatable in the direction of the arrow A of FIG. 4 relative to the base 211. At this time, the subject can therefore insert the wrist while rotating the measurement unit 220 in the direction indicated by the arrow A of FIG. 4. By the measurement unit 220 being configured in this way to be rotatable, the subject can insert the wrist while appropriately changing the direction of the measurement unit 220 in accordance with the positional relationship between the subject and the electronic device 100 of the second example. This makes it easier for the subject to wear the electronic device 100 of the second example.

Figure 7:
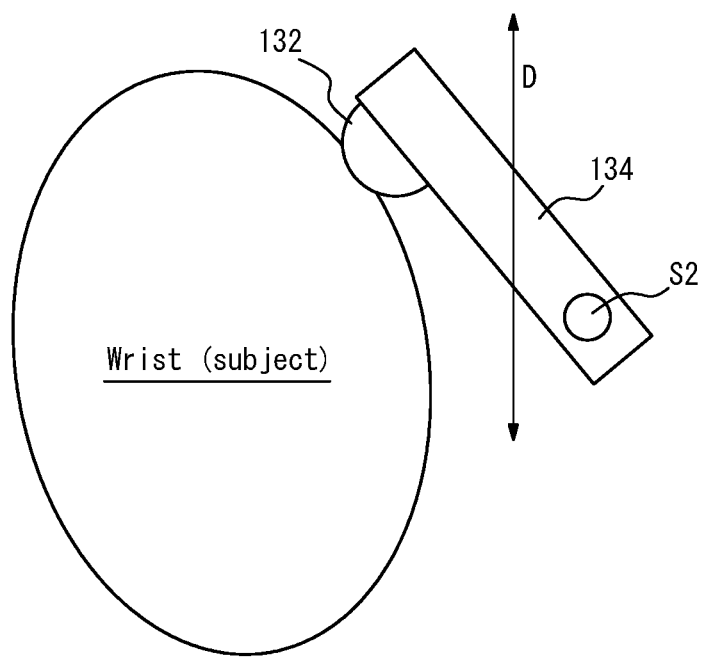
FIG. 7 schematically illustrates the positional relationship between the wrist of the subject and a first arm of the sensor in a front view.

After inserting the wrist into the space formed by the wearing portion 210, the base 211, and the measurement unit 220, the subject places the pulse pad 132 in contact with the skin above the radial artery of the wrist. The body 221 is configured to be displaceable in the direction of the arrow D of FIG. 4. The first arm 134 of the sensor 130 connected to the body 221 is therefore also displaceable in the direction of the arrow D, which is the z-axis direction, as illustrated in FIG. 7. Therefore, the subject can displace the first arm 134 in the direction of the arrow D in accordance with the size, thickness, and the like of the subject's wrist so that the pulse pad 132 comes into contact with the skin above the radial artery. The subject can fix the body 221 at the position of displacement. The electronic device 100 of the second example thus facilitates adjustment of the position of the sensor 130 to a suitable position for measurement. The electronic device 100 of the second example thereby improves measurement accuracy. The body 221 has been described as displaceable in the z-axis direction in the example in FIG. 4, but the body 221 is not necessarily configured to be displaceable in the z-axis direction. It suffices for the body 221 to be configured to be capable of adjusting the position in accordance with the size, thickness, and the like of the wrist, for example. The body 221 may, for example, be configured to be displaceable in a direction intersecting the xy plane, which is the surface of the base 211.

When the pulse pad 132 is in contact with the skin above the radial artery in a direction orthogonal to the skin surface, the pulsation transmitted to the first arm 134 increases. In other words, when the displacement direction of the pulse pad 132 (the direction indicated by the arrow E of FIG. 6) is a direction orthogonal to the skin surface, the pulsation transmitted to the first arm 134 increases, and the accuracy with which pulsation is acquired can increase. In the electronic device 100 of the second example, the body 221 and the sensor 130 connected to the body 221 are configured to be rotatable about the shaft 224 with respect to the exterior portion 222, as indicated by the arrow C of FIG. 4. The subject can thereby adjust the direction of the sensor 130 so that the displacement direction of the pulse pad 132 is a direction orthogonal to the skin surface. In other words, the electronic device 100 of the second example enables adjustment of the direction of the sensor 130 so that the displacement direction of the pulse pad 132 is a direction orthogonal to the skin surface. The electronic device 100 of the second example thereby enables adjustment of the direction of the sensor 130 in accordance with the shape of the subject's wrist. This facilitates transmission of a change in the pulsation of the subject to the first arm 134. The electronic device 100 of the second example thereby improves measurement accuracy.

Figure 8A:
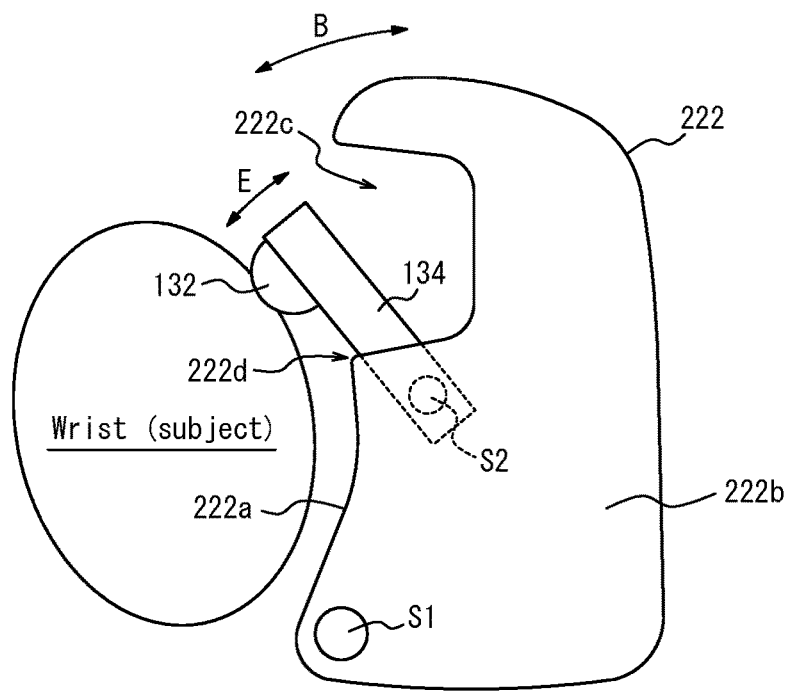
FIG. 8A schematically illustrates the positional relationship between the wrist of the subject, the first arm of the sensor, and the exterior portion of the measurement unit in a front view.
Figure 8B:
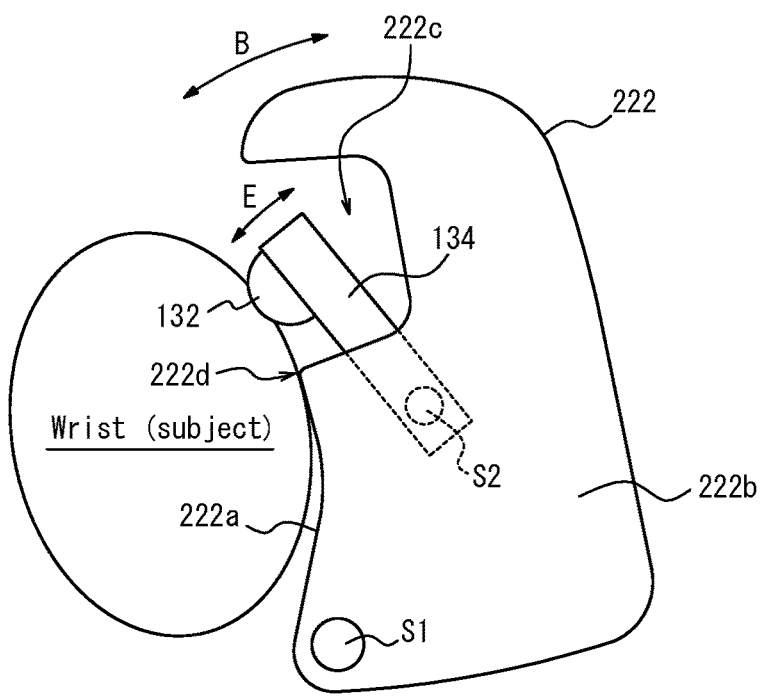
FIG. 8B schematically illustrates the positional relationship between the wrist of the subject, the first arm of the sensor, and the exterior portion of the measurement unit in a front view.

The subject places the pulse pad 132 in contact with the skin above the radial artery of the wrist, as illustrated in FIG. 8A, and then pulls the other end 210b of the wearing portion 210 to fix the wrist to the electronic device 100 of the second example. The exterior portion 222 is configured to be rotatable in the direction of the arrow B in FIG. 4. Therefore, when the subject pulls the wearing portion 210, the exterior portion 222 rotates about the shaft S1, and the upper end is displaced in the negative direction of the y-axis. In other words, the upper end of the exterior portion 222 is displaced in the negative direction of the y-axis, as illustrated in FIG. 8B. The first arm 134 is connected to the second arm 135 via the elastic body 140. Therefore, when the upper end of the exterior portion 222 is displaced in the negative direction of the y-axis, the pulse pad 132 is biased towards the radial artery by the elastic force of the elastic body 140. Consequently, the pulse pad 132 can more reliably capture changes in the pulse. The electronic device 100 of the second example thereby improves measurement accuracy.

The rotation direction of the exterior portion 222 (the direction indicated by arrow B) and the rotation direction of the first arm 134 (the direction indicated by the arrow E) may be substantially parallel. As the rotation direction of the exterior portion 222 and the rotation direction of the first arm 134 are closer to being parallel, the elastic force of the elastic body 140 acts more efficiently on the first arm 134 when the upper end of the exterior portion 222 is displaced in the negative direction of the y-axis. The range over which the rotation direction of the exterior portion 222 and the rotation direction of the first arm 134 are substantially parallel includes the range over which the elastic force of the elastic body 140 acts on the first arm 134 when the upper end of the exterior portion 222 is displaced in the negative direction of the y-axis.

Here, the surface 222b on the front side of the exterior portion 222 illustrated in FIG. 8A is substantially rectangular, with the long sides in the up-down direction. The surface 222b includes a notch 222c at the upper end on the side in the negative direction of the y-axis. The notch 222c makes the surface 222b less likely to contact the skin above the radial artery when the upper end of the exterior portion 222 is displaced in the negative direction of the y-axis, as illustrated in FIG. 8B. This helps to prevent pulsation of the radial artery from being hindered by contact with the surface 222b.

Furthermore, when the upper end of the exterior portion 222 is displaced in the negative direction of the y-axis as illustrated in FIG. 8B, the end 222*d* at the lower side of the notch 222*c* contacts the wrist at a different position than the radial artery. When the end 222*d* comes into contact with the wrist, the exterior portion 222 is no longer displaced in the negative direction of the y-axis beyond the contact position. The end 222*d* can therefore prevent the exterior portion 222 from being displaced beyond a predetermined position. If the exterior portion 222 were displaced in the negative direction of the y-axis beyond a predetermined position, the first arm 134 would be strongly pressed towards the radial artery by the elastic force of the elastic body 140. Pulsation of the radial artery would therefore tend to be hindered. Since the exterior portion 222 includes the end 222*d*, the electronic device 100 of the second example can prevent an excessive pressure from acting on the radial artery from the first arm 134, making the pulsation of the radial artery less likely to be hindered. In this way, the end 222*d* functions as a stopper that restricts the range over which the exterior portion 222 is displaceable.

In the present embodiment, the rotation shaft S2 of the first arm 134 may be disposed at a position away from the side of the surface 222*b* in the negative direction of the y-axis, as illustrated in FIG. 8A. When the rotation shaft S2 is disposed near the side of the surface 222*b* in the negative direction of the y-axis, the changes in pulsation of the radial artery might not be captured accurately due to the first arm 134 touching the subject's wrist. The position of the rotation shaft S2 away from the side of the surface 222*b* in the negative direction of the y-axis can reduce the probability of the first arm 134 touching the wrist, thereby making it easier for the first arm 134 to capture changes in pulsation more accurately.

The subject pulls the other end 210*b* of the wearing portion 210 and fixes the wearing portion 210 with the fixing mechanism of the fixing portion 212 to wear the electronic device 100 of the second example on the wrist. Once worn on the wrist in this way, the electronic device 100 of the second example measures the subject's pulse wave by the first arm 134 changing in the direction indicated by the arrow E together with changes in pulsation.

The above-described first and second examples of the electronic device 100 merely illustrate example configurations of the electronic device 100. The electronic device 100 is therefore not limited to the configurations illustrated by the first and second examples. It suffices for the electronic device 100 to include a configuration capable of measuring the subject's pulse wave.

Figure 9:
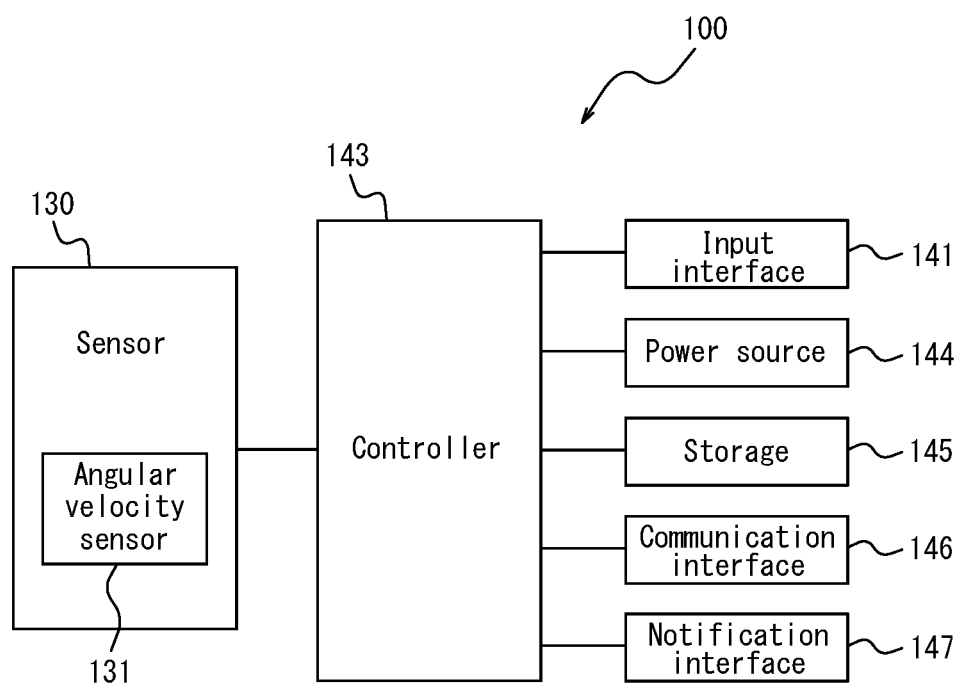
FIG. 9 is a functional block diagram of an electronic device.

FIG. 9 is a functional block diagram of the electronic device 100 of the first or second example. The electronic device 100 includes the sensor 130, the input interface 141, a controller 143, a power source 144, a storage 145, a communication interface 146, and a notification interface 147. In the electronic device 100 of the first example, the controller 143, power source 144, storage 145, communication interface 146, and notification interface 147 may be included inside the measurement unit 120 or the wearing portion 110. In the electronic device 100 of the second example, the controller 143, power source 144, storage 145, communication interface 146, and notification interface 147 may be included inside the fixing portion 212.

The sensor 130 includes the angular velocity sensor 131, detects pulsation from the measured part, and acquires the pulse wave.

The controller 143 is a processor that, starting with the functional blocks of the electronic device 100, controls and manages the electronic device 100 overall. Furthermore, the controller 143 is a processor that, using the acquired pulse wave, estimates the blood glucose level of the subject. The controller 143 is configured by a processor, such as a central processing unit (CPU), that executes programs prescribing control procedures and programs for estimating the blood glucose level of the subject. These programs may, for example, be stored on a storage medium such as the storage 145. Based on an index calculated from the pulse wave, the controller 143 estimates a state related to the subject's glucose metabolism, lipid metabolism, or the like. The controller 143 may notify the notification interface 147 of data.

The power source 144 for example includes a lithium-ion battery and a control circuit for charging and discharging the battery. The power source 144 supplies power to the electronic device 100 overall. The power source 144 is not limited to being a secondary cell such as a lithium-ion battery and may, for example, be a primary cell such as a button cell.

The storage 145 stores programs and data. The storage 145 may include a non-transitory storage medium, such as a semiconductor storage medium or a magnetic storage medium. The storage 145 may also include a plurality of types of storage media. The storage 145 may include a combination of a portable storage medium, such as a memory card, optical disc, or magneto-optical disc, and an apparatus for reading the storage medium. The storage 145 may include a storage device used as a volatile storage area, such as random access memory (RAM). The storage 145 stores a variety of information, programs for causing the electronic device 100 to operate, and the like and also functions as a working memory. The storage 145 may, for example, store the measurement result of the pulse wave acquired by the sensor 130.

The communication interface 146 exchanges a variety of data with an external apparatus by wired or wireless communication. For example, the communication interface 146 communicates with an external apparatus that stores the biological information of the subject to manage the state of health. The communication interface 146 transmits, to the external apparatus, the measurement result of the pulse wave measured by the electronic device 100 and the state of health estimated by the electronic device 100.

The notification interface 147 provides notification of information by sound, vibration, images, and the like. The notification interface 147 may include a speaker, a vibration unit, and a display device. The display device can, for example, be a liquid crystal display (LCD), an organic electro-luminescence display (OELD), an inorganic electro-luminescence display (IELD), or the like. In an embodiment, the notification interface 147 provides notification of the state of the subject's glucose metabolism or lipid metabolism.

The electronic device 100 according to an embodiment estimates the state of glucose metabolism. In an embodiment, the electronic device 100 estimates the blood glucose level as the state of glucose metabolism.

The electronic device 100 estimates the subject's blood glucose level based on an estimation formula derived by regression analysis, for example. The electronic device 100 stores the estimation formula for estimating the blood glucose level based on the pulse wave in the storage 145, for example, in advance. The electronic device 100 estimates the blood glucose level using this estimation formula.

Estimation theory related to estimating the blood glucose level based on the pulse wave is now described. As a result of an increase in the blood glucose level after a meal, the blood fluidity reduces (viscosity increases), blood vessels dilate, and the amount of circulating blood increases. Vascular dynamics and hemodynamics are determined so as to balance these states. The reduction in blood fluidity occurs, for example, because of an increase in the viscosity of blood plasma or a reduction in the deformability of red blood cells. Dilation of blood vessels occurs for reasons such as secretion of insulin, secretion of digestive hormones, and a rise in body temperature. When blood vessels dilate, the pulse rate increases to suppress a reduction in blood pressure. Furthermore, the increase in the amount of circulating blood compensates for blood consumption for digestion and absorption. The postprandial vascular dynamics and hemodynamics due to these causes are also reflected in the pulse wave. The electronic device 100 can therefore estimate the blood glucose level based on the pulse wave.

An estimation formula for estimating the blood glucose level based on the above estimation theory can be derived by performing regression analysis on sample data of postprandial pulse waves and blood glucose levels obtained from a plurality of subjects. By applying the derived estimation formula to the index in accordance with the subject's pulse wave at the time of estimation, the subject's blood glucose level can be estimated. If the estimation formula is derived in particular by performing regression analysis using sample data for which variation in the blood glucose level is close to a normal distribution, the blood glucose level of the subject being tested can be estimated. The estimation formula may, for example, be derived by partial least squares (PLS) regression analysis. In PLS regression analysis, a regression coefficient matrix is calculated by using the covariance of the outcome variable (feature amount of the estimation target) and the explanatory variable (feature amount used for estimation) to perform multiple regression analysis by adding to the variable in order from the component with the highest correlation between the outcome variable and the explanatory variable.

"Preprandial" as used in the present disclosure refers to before a meal is taken, such as when fasting. "Postprandial" as used in the present disclosure refers to a time after a meal is taken, such as the time when the effects of the meal are reflected in the blood at a predetermined time after the meal is taken. As described in the present embodiment, "postprandial" in the case of the electronic device 100 estimating the blood glucose level may refer to the time at which the blood glucose level increases (for example, approximately one hour after the start of the meal).

Figure 10:
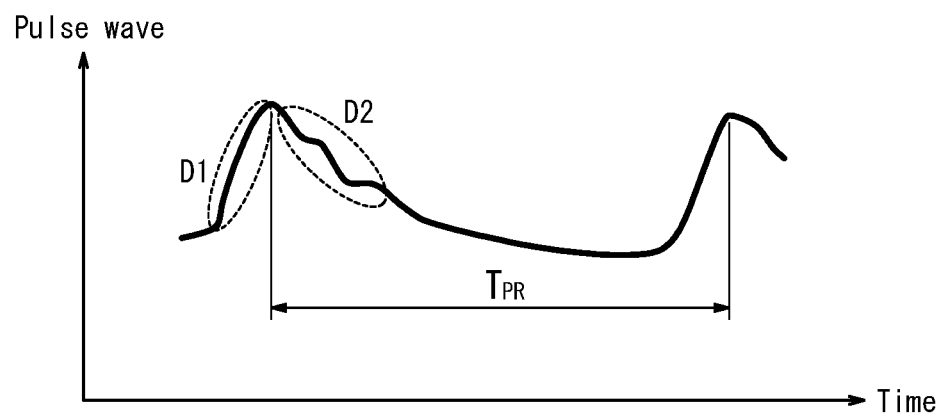
FIG. 10 illustrates an example of an estimation method based on pulse waves in an electronic device.

FIG. 10 illustrates an example pulse wave to illustrate an example of an estimation method based on pulse waves. The estimation formula for estimating blood glucose level is, for example, derived by regression analysis related to age, an index SI indicating the rising of a pulse wave (rising index), an augmentation index (AI), and pulse rate PR.

Figure 11:
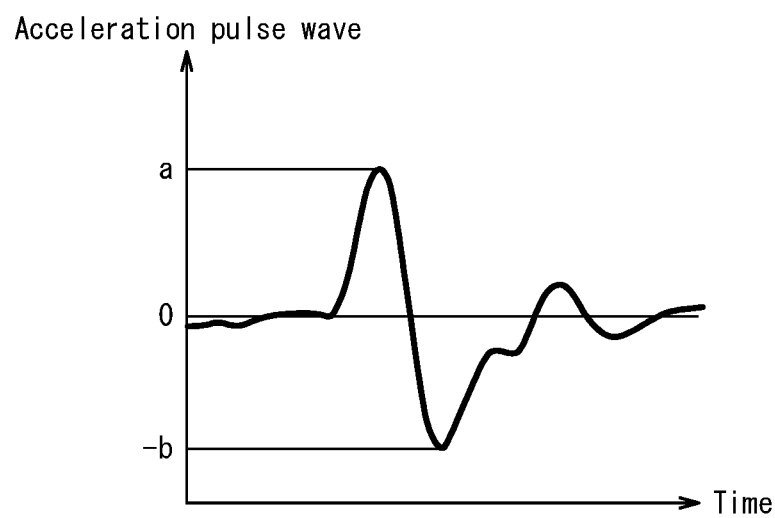
FIG. 11 illustrates an example of the acceleration pulse wave.

The rising index SI is derived in accordance with the waveform indicated in the area D1 of FIG. 10. In greater detail, the rising index SI is the ratio of the first local minimum to the first local maximum in the acceleration pulse wave yielded by the second derivative of the pulse wave. For example, for the acceleration pulse wave illustrated as an example in FIG. 11, the rising index SI is expressed as b/a. The rising index SI decreases because of a reduction in fluidity of the blood, secretion of insulin, dilation (relaxation) of blood vessels due to increased body temperature, and the like after a meal. In the acceleration pulse wave b/a, b is negative, and a is positive. In this case, b/a is negative. A smaller value of b/a means that b is growing in the negative direction.

Figure 12:
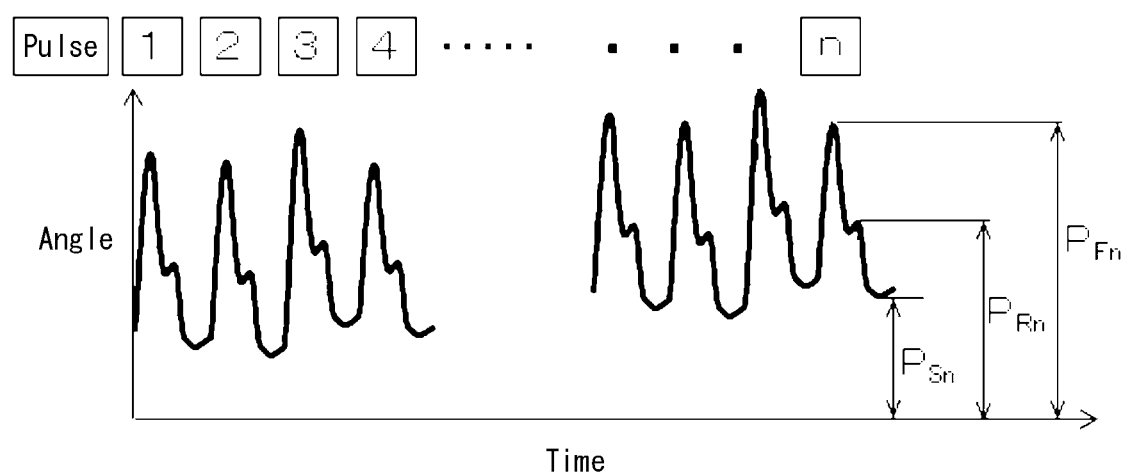
FIG. 12 illustrates an example of pulse waves acquired by a sensor.

The AI is an index represented by the ratio between the magnitudes of the forward wave and the reflected wave of the pulse wave. A method of deriving AI is described with reference to FIG. 12, which illustrates an example of pulse waves acquired at the wrist using the electronic device 100. FIG. 12 illustrates the case of using the angular velocity sensor 131 as means for detecting the pulsation. FIG. 12 is a time integration of the angular velocity acquired by the angular velocity sensor 131, with the horizontal axis representing time and the vertical axis representing the angle. Since the acquired pulse wave may, for example, include noise that is due to body movement of the subject, the pulse wave may be corrected by a filter that removes the direct current (DC) component, so as to extract only the pulsation component.

Propagation of the pulse wave is a phenomenon in which pulsation due to blood extruded from the heart is transmitted through artery walls or blood. The pulsation due to blood pumped from the heart reaches the peripheries of limbs as a forward wave, a portion of which is reflected at locations such as where a blood vessel branches, or where the diameter of a blood vessel changes, and returns as a reflected wave. AI is the quotient when the magnitude of the reflected wave is divided by the magnitude of the forward wave and is expressed as $AIn=(PRn-PSn)/(PFn-PSn)$. Here, AIn is the AI for each pulse beat. AI may, for example, be calculated by measuring the pulse wave for several seconds and calculating the average AIave of the AIn for each pulse beat (n=an integer from 1 to n). The AI is derived from the waveform indicated in area D2 of FIG. 10. The AI reduces because of a reduction in fluidity of the blood, dilation of blood vessels due to increased body temperature, and the like after a meal.

The pulse rate PR is derived from the period TPR of the pulse wave illustrated in FIG. 10. The pulse rate PR rises after a meal.

The electronic device 100 can estimate the blood glucose level using the estimation formula derived from the rising index SI, the AI, and the pulse rate PR.

Figure 13A:
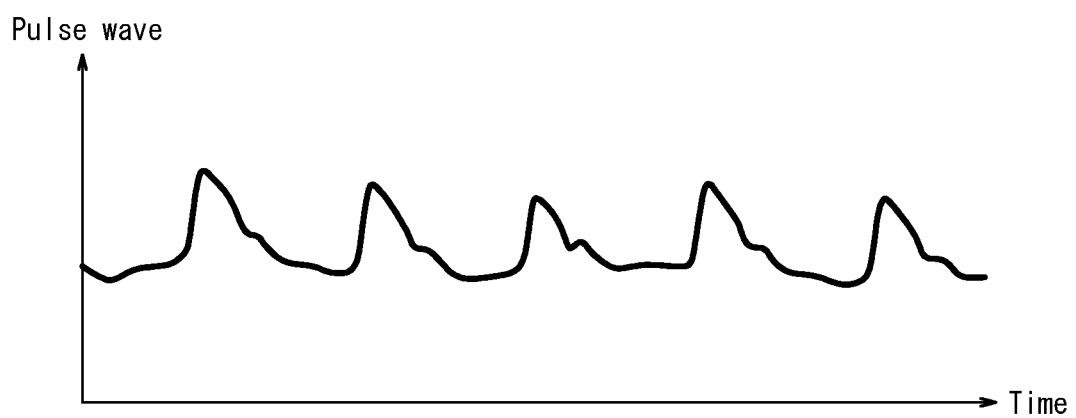
FIG. 13A illustrates an example of an estimation method, based on a change in pulse waves, in an electronic device.
Figure 13B:
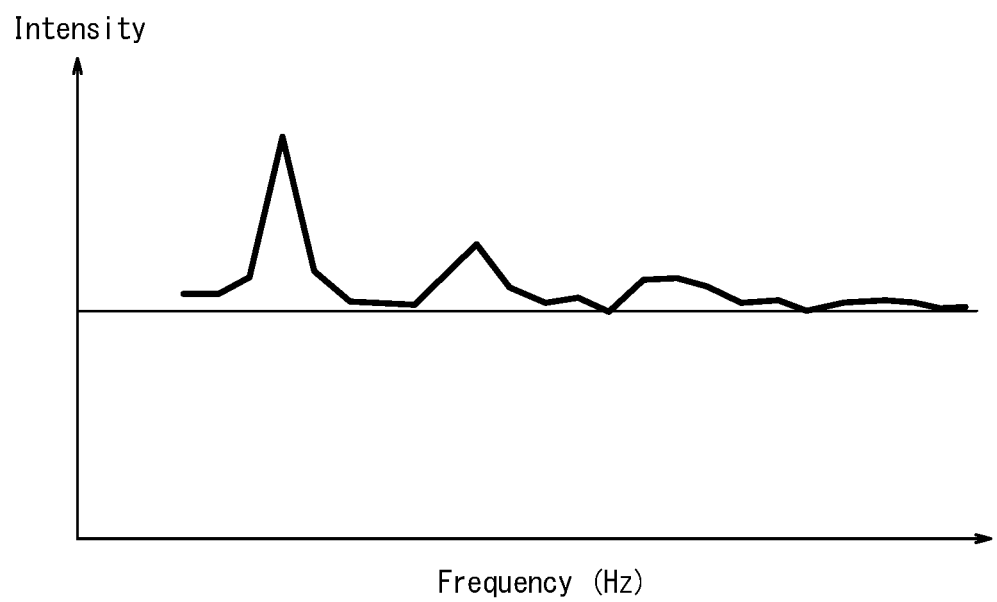
FIG. 13B illustrates another example of an estimation method, based on a change in pulse waves, in an electronic device.

FIGS. 13A and 13B illustrate another example of an estimation method based on pulse waves. FIG. 13A illustrates a pulse wave, and FIG. 13B illustrates the result of performing a fast Fourier transform (FFT) on the pulse wave of FIG. 13A. The estimation formula for estimating the blood glucose level is, for example, derived by regression analysis related to a fundamental and harmonic component (Fourier coefficients) that are derived by an FFT. The peak value in the result of the FFT illustrated in FIG. 13B changes in accordance with change in the waveform of the pulse wave. Therefore, the blood glucose level can be estimated with an estimation formula derived using the Fourier coefficients.

Based on the above-described rising index SI, AI, pulse rate PR, Fourier coefficients, and the like, the electronic device 100 uses the estimation formula to estimate the blood glucose level of the subject.

Here, a method for deriving an estimation formula for the case of the electronic device 100 estimating the subject's blood glucose level is described. The estimation formula need not be derived by the electronic device 100 and may be derived in advance using another computer or the like. In the present disclosure, the device that derives the estimation formula is referred to as an estimation formula derivation apparatus. The derived estimation formula is, for example, stored in the storage 145 in advance, before the subject estimates the blood glucose level with the electronic device 100.

Figure 14:
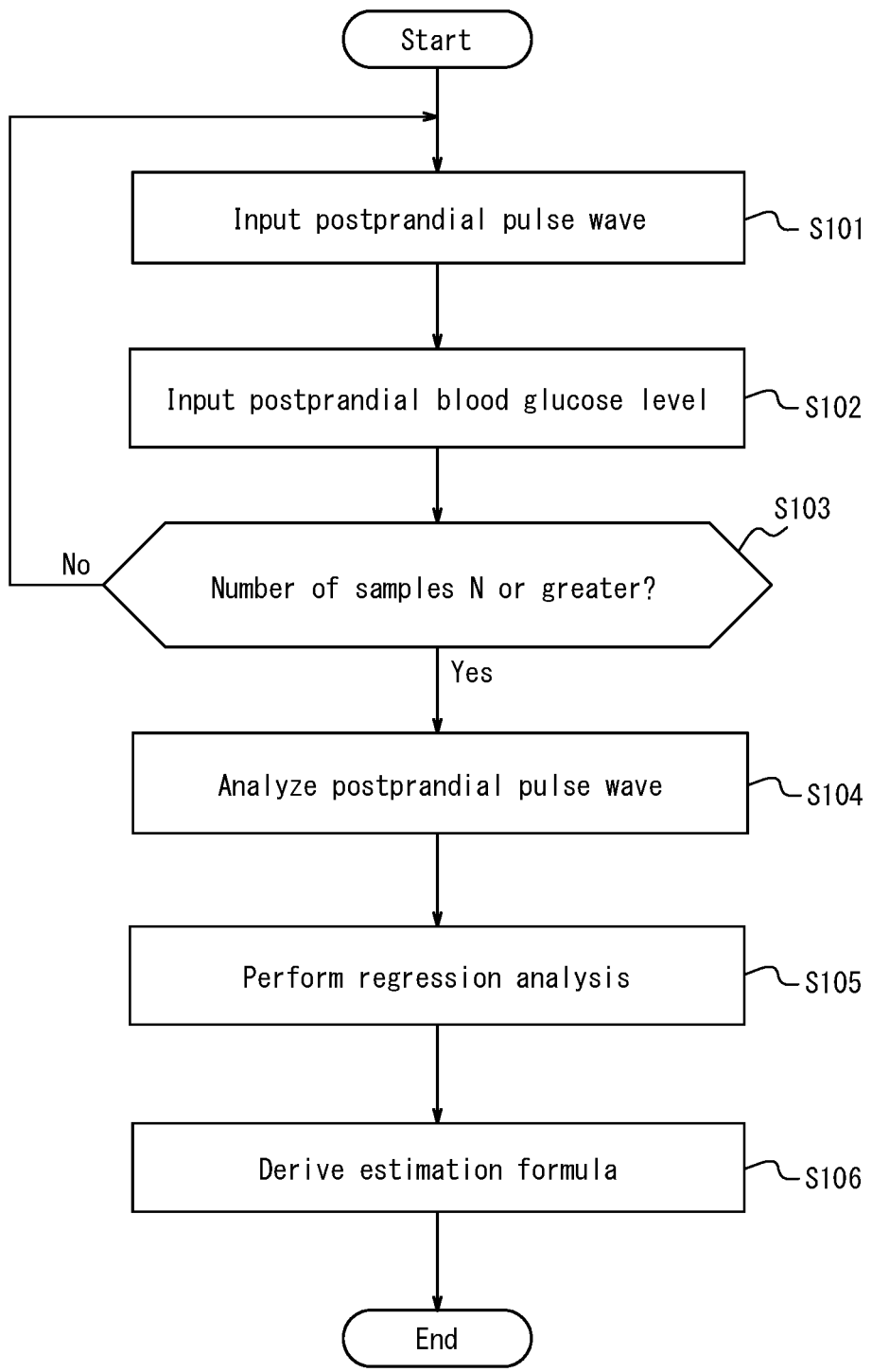
FIG. 14 is a flowchart for deriving an estimation formula used by the electronic device of FIG. 1.

FIG. 14 is a flowchart for deriving an estimation formula used by the electronic device 100. The estimation formula is derived by performing regression analysis based on sample data obtained by measuring a subject's postprandial pulse wave using a pulse wave meter and measuring the subject's postprandial blood glucose level using a blood glucose meter. The acquired sample data are not limited to after a meal. It suffices to use data for time slots with large variation in the blood glucose level.

During derivation of the estimation formula, first, information related to the subject's postprandial pulse wave, as measured by a pulse wave meter, is inputted into the estimation formula derivation apparatus (step S101).

Information related to the subject's postprandial blood glucose level, as measured by a blood glucose meter, is also inputted into the estimation formula derivation apparatus (step S102). The blood glucose level inputted in step S102 is, for example, measured with a blood glucose meter by taking a blood sample. The age of the subject for each set of sample data may also be inputted in step S101 or step S102.

The estimation formula derivation apparatus determines whether the number of samples in the sample data inputted in step S101 and step S102 is N or greater, which is an amount sufficient for regression analysis (step S103). The sample number N can be determined appropriately and can be 100, for example. When determining that the number of samples is less than N (No), the estimation formula derivation apparatus repeats step S101 and step S102 until the number of samples becomes N or greater. Conversely, when determining that the number of samples is N or greater (Yes), the estimation formula derivation apparatus proceeds to step S104 and calculates the estimation formula.

During calculation of the estimation formula, the estimation formula derivation apparatus analyzes the inputted postprandial pulse wave (step S104). For example, the estimation formula derivation apparatus analyzes the rising index SI, the AI, and the pulse rate PR of the postprandial pulse wave. The estimation formula derivation apparatus may analyze the pulse wave by performing FFT analysis.

The estimation formula derivation apparatus then performs regression analysis (step S105). The outcome variable in the regression analysis is the postprandial blood glucose level. The explanatory variables in the regression analysis are, for example, the age inputted in step S101 or step S102 and the rising index SI, the AI, and the pulse rate PR of the postprandial pulse wave analyzed in step S104. When the estimation formula derivation apparatus performs FFT analysis in step S104, the explanatory variables may, for example, be Fourier coefficients calculated as the result of the FFT analysis.

The estimation formula derivation apparatus derives an estimation formula for estimating the postprandial blood glucose level based on the result of regression analysis (step S106).

Figure 15:
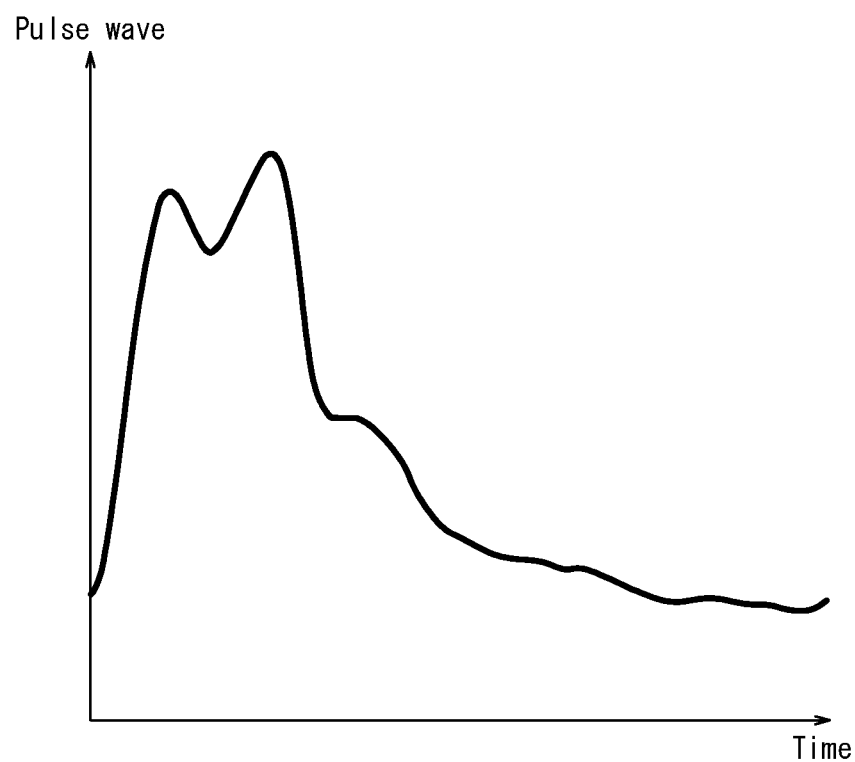
FIG. 15 illustrates an example pulse wave.
Figure 16:
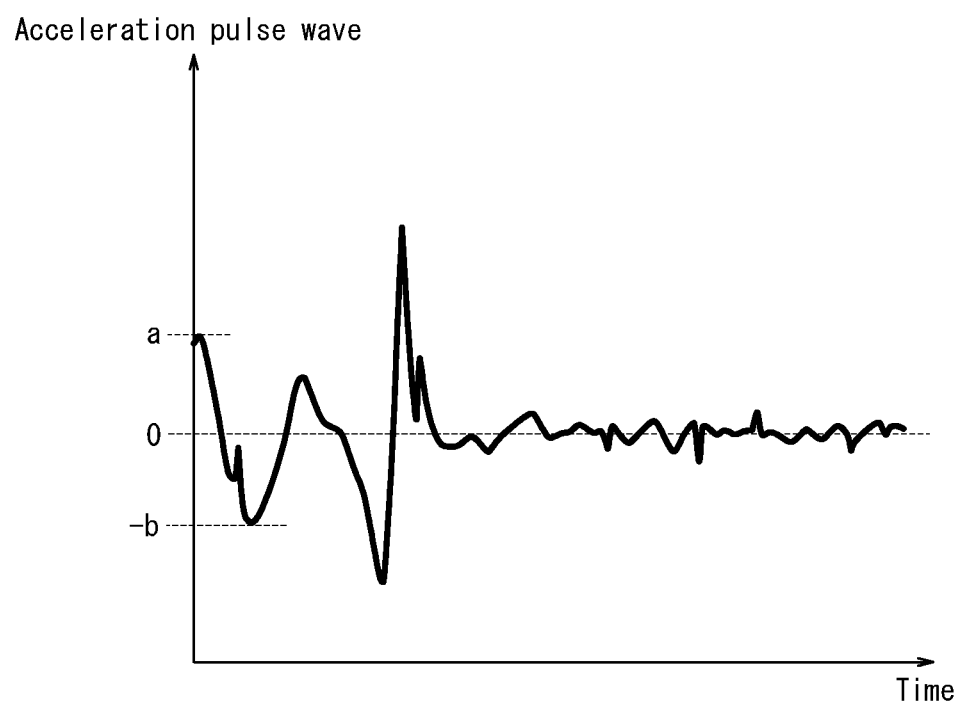
FIG. 16 illustrates an example of the acceleration pulse wave.

Depending on the waveform of the pulse wave, the AI may be difficult to detect. FIG. 15 illustrates an example pulse wave. The pulse wave illustrated in FIG. 15 is greatly affected by the reflected wave, represented by the second peak. FIG. 16 illustrates the acceleration pulse wave of the pulse wave illustrated in FIG. 15. The effect of the reflected wave also appears in the waveform of the acceleration pulse wave, as illustrated in FIG. 16, for example. When AI becomes small, AI may be difficult to detect or may disappear and be undetectable. Examples of when AI becomes small are when blood vessels dilate or the blood glucose level is high.

Figure 17:
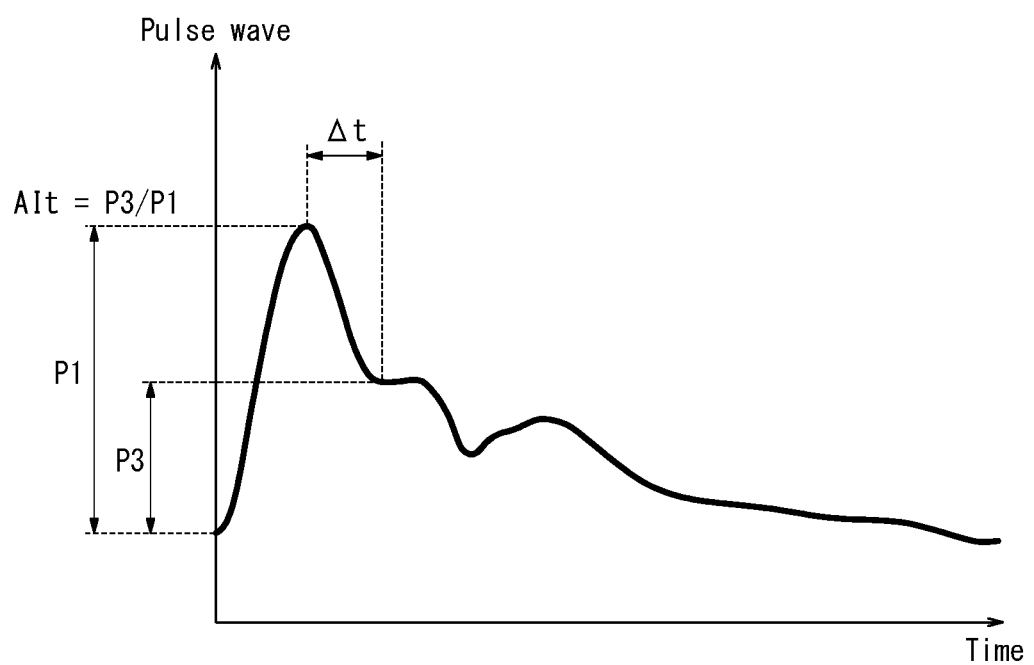
FIG. 17 illustrates an example pulse wave.

Therefore, instead of or in addition to the AI, the estimation formula may be derived using another index. The use of another index AIt is now described as an example. AIt is the rate of change in the pulse wave at a predetermined time after the peak of the pulse wave. FIG. 17 illustrates an example pulse wave to illustrate the AIt. The AIt is the ratio of P3 to P1, where P1 is the height of the peak of the pulse wave, and P3 is the height of the pulse wave after a predetermined time $\Delta t$ from the point in time when P1 appears. In other words, AIt=P3/P1. The predetermined time $\Delta t$ may be a time before the effect of the reflected wave appears. For example, if the pulse wave velocity is 10 m/sec, and the distance from the heart to the main reflection point inside the body is 1 m round trip, then the time until the reflected wave makes a round trip is 100 msec. The predetermined time $\Delta t$ may, for example, be 100 msec calculated in this way. In other words, suppose the main reflection point of the reflected wave of AI is the abdominal aortic bifurcation. Also suppose that the round-trip distance between the heart and the abdominal aortic bifurcation is 2L, and the pulse wave velocity is PWV. This yields $\Delta t$=2L/PWV. The pulse wave velocity of the abdominal aorta is generally thought to be 10 m/sec. The value of L is generally 50 cm. Accordingly, $\Delta t$=2L/PWV=100/1000=0.1 sec.

Naturally, the predetermined time $\Delta t$ may vary depending on individual differences in the round-trip distance 2L and the pulse wave velocity PWV, the measurement time, the state of health, or other factors. For example, the round-trip distance 2L and the pulse wave velocity PWV may vary from the aforementioned example values due to age, sex, health status, or other factors. The predetermined time $\Delta t$ may therefore vary from 100 msec and may be a numerical value in a certain range. For example, the predetermined time $\Delta t$ may be 100 msec or less, or 100 msec or more. Setting the predetermined time $\Delta t$ in this way facilitates accurate calculation of the AIt even when the reflected wave disappears. Depending on the waveform of the pulse wave, the use of AIt as an index related to pulse wave can improve the estimation accuracy of the subject's blood glucose level as compared to when AI is used. The predetermined time $\Delta t$ is the time around which the reflected wave appears. The effect of the reflected wave is often included in the AIt.

Figure 18A:
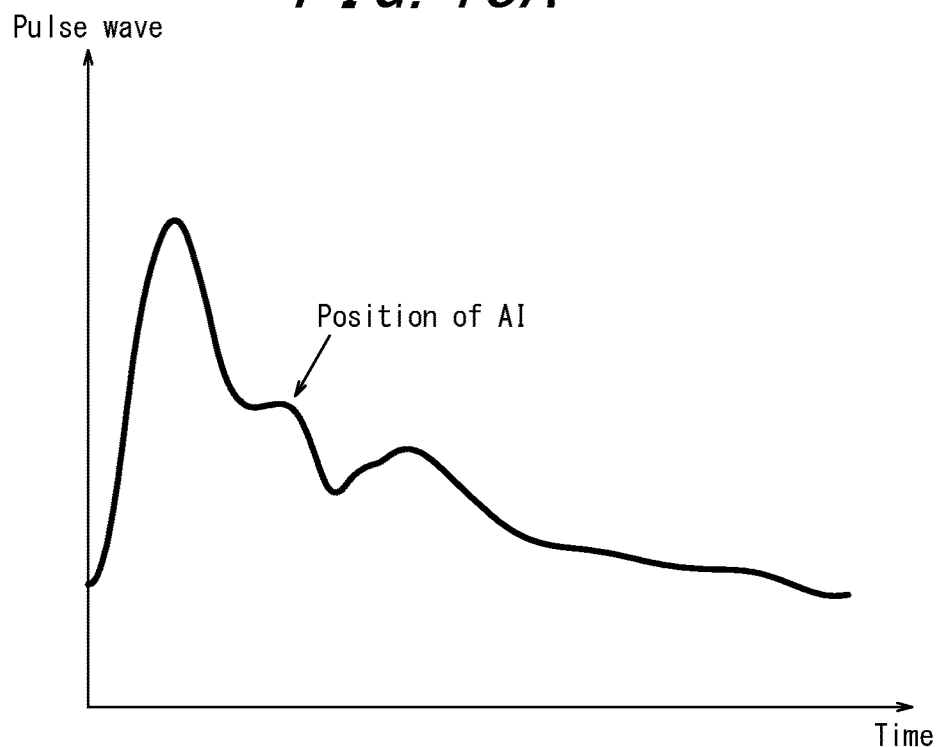
FIG. 18A is a graph illustrating the preprandial pulse waveform in the present embodiment.
Figure 18B:
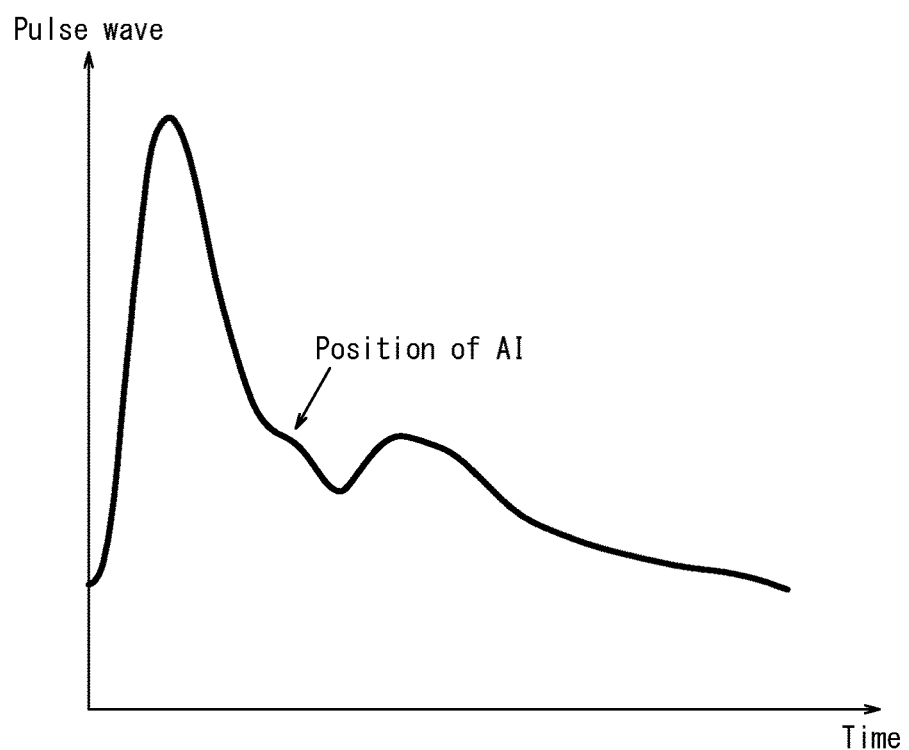
FIG. 18B is a graph illustrating the postprandial pulse waveform in the present embodiment.

With reference to FIGS. 18A and 18B, the change from the preprandial pulse waveform to the postprandial pulse waveform is now described. FIGS. 18A and 18B are graphs illustrating the change from the preprandial pulse waveform to the postprandial pulse waveform in the present embodiment. In FIGS. 18A and 18B, the horizontal axis represents time, and the vertical axis represents the pulse wave. FIG. 18A is the preprandial pulse waveform, and FIG. 18B is the pulse waveform one hour after a meal. Both pulse waveforms are for the pulse wave of the same individual. As illustrated in FIG. 18B, the postprandial AI may become small and difficult to detect. As the blood glucose level increases, AI further decreases or disappears.

The estimation formula derivation apparatus can derive an estimation formula with the flowchart described with reference to FIG. 14, using the AIt as one explanatory variable. In the present embodiment, the estimation formula derivation apparatus is described below as deriving an estimation formula with the above-described age, rising index SI, AI, pulse rate PR, and also AIt as explanatory variables.

The estimation formula is not necessarily derived by PLS regression analysis. The estimation formula may be derived using another method. For example, the estimation formula may be derived by neural network regression analysis.

Figure 19:
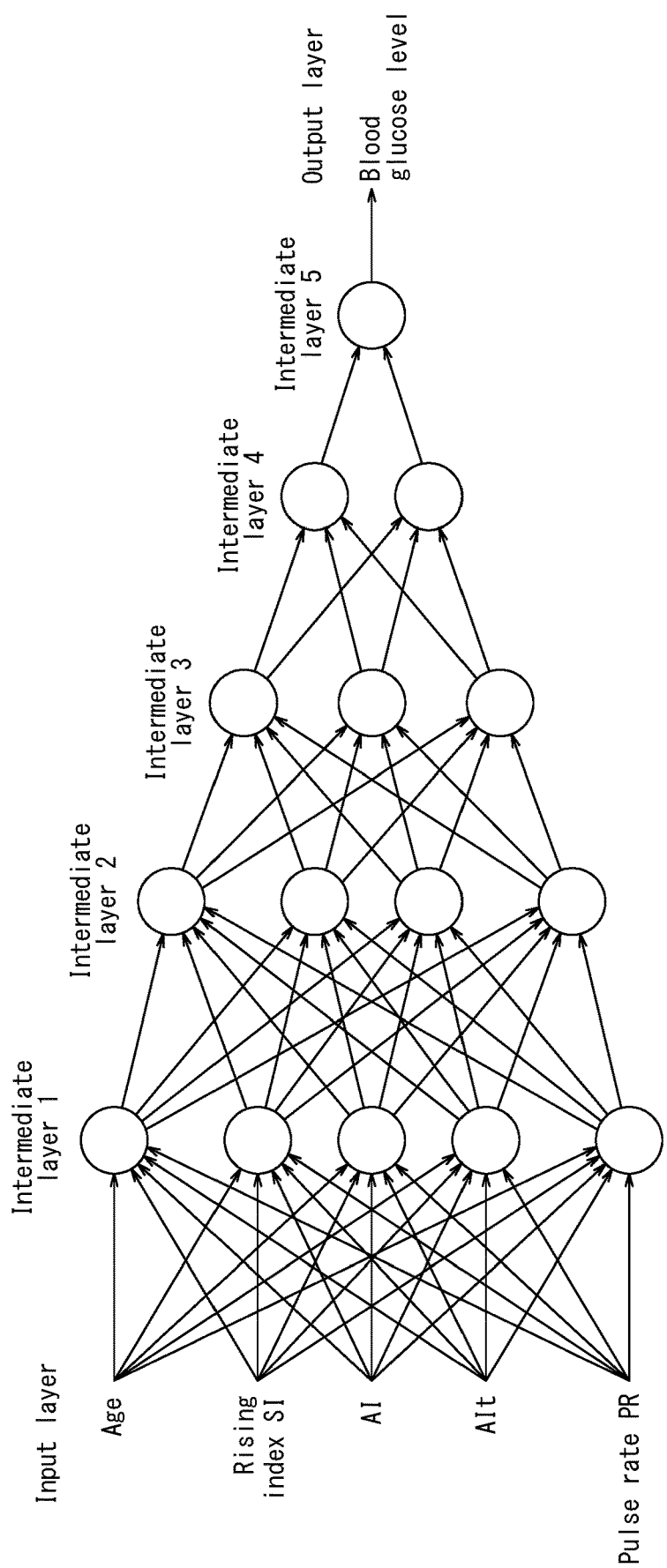
FIG. 19 illustrates an example of neural network regression analysis.

FIG. 19 illustrates an example of neural network regression analysis. FIG. 19 schematically illustrates a neural network in which the input layer is five neurons and the output layer is one neuron. The five neurons of the input layer are age, rising index SI, AI, AIt, and pulse rate PR. The neuron of the output layer is the blood glucose level. The neural network illustrated in FIG. 19 includes five intermediate layers between the input layer and the output layer: intermediate layer 1, intermediate layer 2, intermediate layer 3, intermediate layer 4, and intermediate layer 5. Intermediate layer 1 has 5 nodes, intermediate layer 2 has 4 nodes, intermediate layer 3 has 3 nodes, intermediate layer 4 has 2 nodes, and intermediate layer 5 has 1 node. Each node of the intermediate layers receives input of the sum of components of data that are outputted from the preceding layer and weighted. Each node of the intermediate layers outputs a value yielded by performing a predetermined calculation (bias) on the inputted data. During neural network regression analysis, backpropagation is used to compare the estimated output value with the correct output value, and the weighting and bias are adjusted in the network to minimize the difference between these two values. The estimation formula can be derived in this way by neural network regression analysis.

Figure 20:
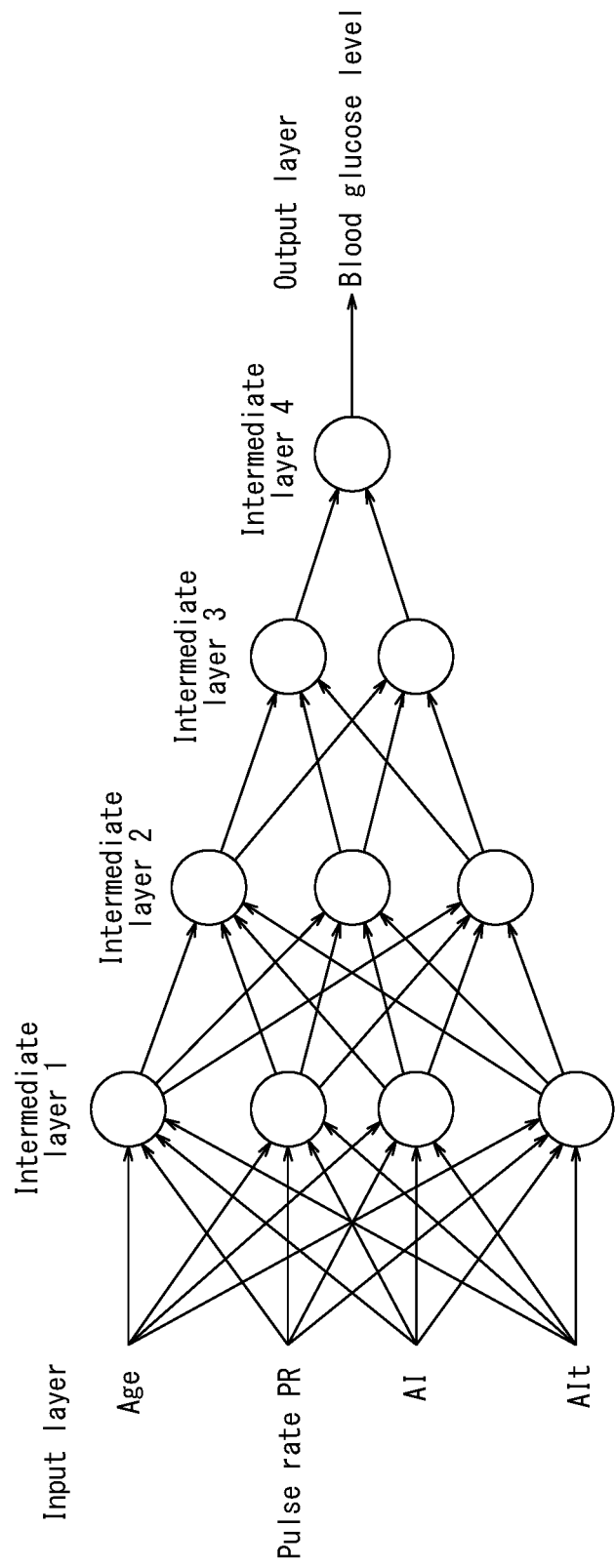
FIG. 20 illustrates an example of neural network regression analysis.

The neural network regression analysis used in the present embodiment is not limited to the case illustrated in FIG. 19. For example, the example of neural network regression analysis illustrated in FIG. 20 may be used. In FIG. 20, the four neurons of the input layer are age, pulse rate PR, AI, and AIt. The neuron of the output layer is the blood glucose level.

Figure 21B:
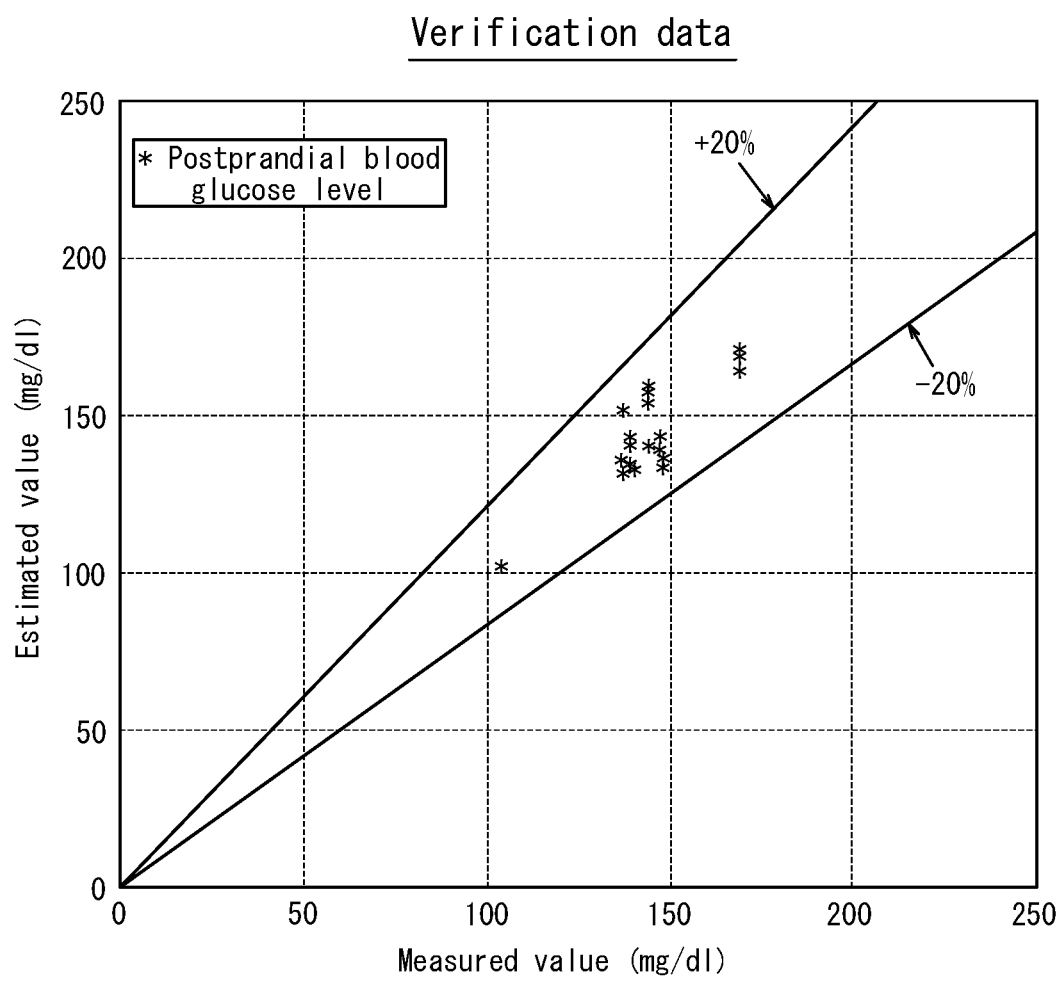
FIG. 21B is a graph illustrating verification data for neural network regression analysis.

FIGS. 21A and 21B illustrate the learning data and verification data used in the neural network regression analysis of the present embodiment illustrated in FIG. 19. FIG. 21A is a graph illustrating learning data for the neural network regression analysis of the present embodiment, and FIG. 21B is a graph illustrating verification data for neural network regression analysis.

Figure 22:
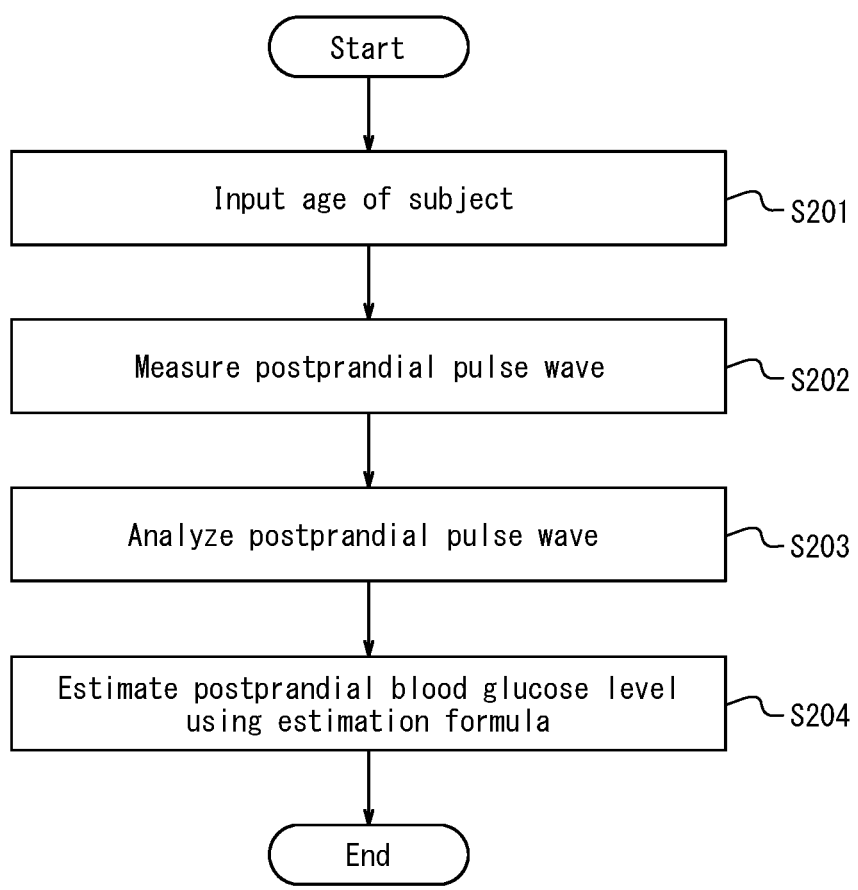
FIG. 22 is a flowchart for estimating a subject's postprandial blood glucose level using an estimation formula.

Next, an example process for estimating the subject's blood glucose level using an estimation formula is described. FIG. 22 is a flowchart for estimating a subject's postprandial blood glucose level using the derived estimation formula.

First, the electronic device 100 receives input of the subject's age based on operation of the input interface 141 by the subject (step S201).

After the subject eats a meal, the electronic device 100 measures the subject's postprandial pulse wave based on operation by the subject (step S202).

The electronic device 100 then analyzes the measured postprandial pulse wave (step S203). For example, the electronic device 100 analyzes the rising index SI, the AI, the AIt, and the pulse rate PR related to the measured postprandial pulse wave.

The electronic device 100 applies the subject's age received as input in step S201 and the rising index SI, the AI, the AIt, and the pulse rate PR analyzed in step S203 to the estimation formula and estimates the subject's postprandial blood glucose level (step S204). The subject is notified of the estimated postprandial blood glucose level by the notification interface 147 of the electronic device 100, for example.

In this way, the electronic device 100 according to the present embodiment uses an estimation formula derived based on the postprandial pulse wave and blood glucose level to estimate the subject's postprandial blood glucose level based on the subject's measured postprandial pulse wave. The electronic device 100 can therefore estimate the postprandial blood glucose level rapidly and in a non-invasive manner. Consequently, the electronic device 100 can easily estimate the subject's state of health.

As an index related to pulse wave, the AIt is not affected by the disappearance of the reflected wave as compared to the AI. Use of the AIt, therefore, can improve the estimation accuracy of the subject's blood glucose level. Even when the reflected wave AI is difficult to detect, the AIt can be detected stably, thereby improving accuracy.

The electronic device 100 is not limited to the postprandial blood glucose level and may estimate the subject's blood glucose level at any timing. The electronic device 100 can also estimate the blood glucose level at any timing rapidly and in a non-invasive manner.

The method of estimating the postprandial blood glucose level by the electronic device 100 is not limited to the above-described method. For example, each time the electronic device 100 estimates the subject's postprandial blood glucose level, the electronic device 100 may select one estimation formula from among a plurality of estimation formulas and estimate the subject's postprandial blood glucose level using the selected estimation formula. A plurality of estimation formulas are derived in advance in this case.

A plurality of estimation formulas may, for example, be derived in accordance with the content of meals. The content of a meal may, for example, include the quantity and quality of the meal. The quantity of the meal may, for example, include the weight of the meal. The quality of the meal may, for example, include the menu item, ingredients (food), cooking method, or the like.

The content of the meal may, for example, be classified into a plurality of categories. The content of the meal may, for example, be classified into the categories of noodles, set meals, bowls, or the like. The same number of estimation formulas as the number of categories of the content of a meal may, for example, be derived. In other words, when the content of the meal is classified into three categories, an estimation formula may be derived in association with each category. In this case, the number of derived estimation formulas is three. The electronic device 100 uses the estimation formula, among the plurality of estimation formulas, corresponding to the content of the subject's meal to estimate the postprandial blood glucose level.

Figure 23:
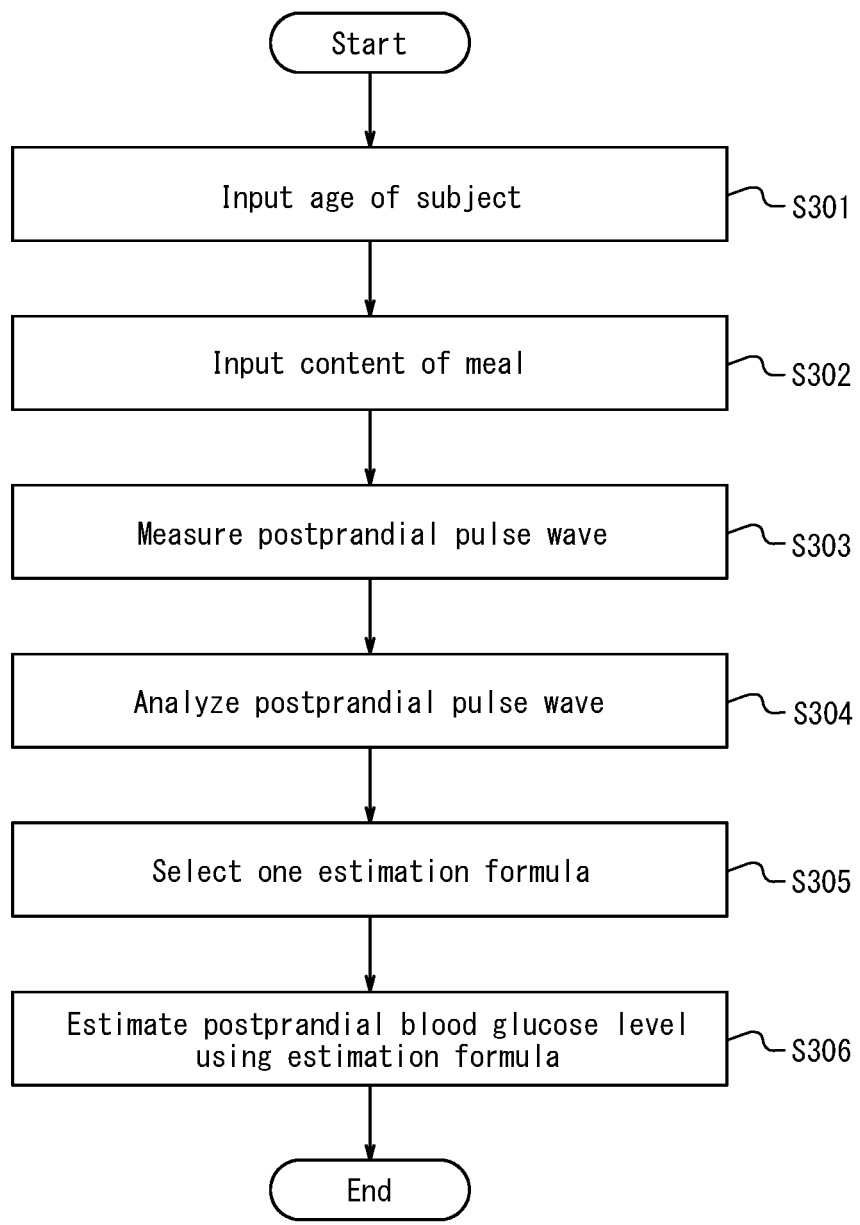
FIG. 23 is a flowchart for estimating a subject's postprandial blood glucose level using a plurality of estimation formulas.

An example process for estimating the subject's blood glucose level using an estimation formula in the case of a plurality of derived estimation formulas is now described. FIG. 23 is a flowchart for estimating a subject's postprandial blood glucose level using a plurality of derived estimation formulas.

The electronic device 100 receives input of the subject's age based on operation of the input interface 141 by the subject (step S301).

The electronic device 100 receives input of the content of the meal based on operation of the input interface 141 by the subject (step S302). The electronic device 100 can receive input of the content of the meal from the subject by various methods. For example, when the electronic device 100 includes a display device, the electronic device 100 may receive input by displaying contents of meals (for example, categories) in a manner selectable by the subject and prompting the subject to select the content of the meal closest to the meal the subject is about to eat. The electronic device 100 may, for example, receive input by having the subject list the content of the meal using the input interface 141. When the electronic device 100 includes an imaging unit such as a camera, the electronic device 100 may, for example, receive input by using the imaging unit to capture an image of the meal about to be eaten. In this case, the electronic device 100 may, for example, estimate the content of the meal by image analysis on the captured image that is received.

The electronic device 100 measures the subject's postprandial pulse wave based on operation by the subject (step S303).

The electronic device 100 analyzes the measured pulse wave (step S304). For example, the electronic device 100 analyzes the rising index SI, the AI, the AIt, and the pulse rate PR related to the measured pulse wave.

The electronic device 100 selects one estimation formula from among the plurality of estimation formulas based on the meal content received in step S302 (step S305). For example, the electronic device 100 selects the estimation formula associated with the category closest to the inputted content of the meal.

The electronic device 100 applies the subject's age received as input in step S301 and the rising index SI, the AI, the AIt, and the pulse rate PR analyzed in step S304 to the estimation formula and estimates the subject's postprandial blood glucose level (step S306). The subject is notified of the estimated postprandial blood glucose level by the notification interface 147 of the electronic device 100, for example.

The postprandial blood glucose level may change depending on the content of the meal. Nevertheless, the electronic device 100 can estimate the blood glucose level more accurately in accordance with the content of the meal by estimating the postprandial blood glucose level using an estimation formula, among a plurality of estimation formulas, that corresponds to the content of the meal.

Second Embodiment

In the first embodiment, the case of the electronic device 100 estimating the subject's postprandial blood glucose level has been described. In the second embodiment, an example of the electronic device 100 estimating the subject's postprandial lipid level is described. Here, the lipid level includes neutral lipids, total cholesterol, HDL cholesterol, LDL cholesterol, and the like. In the description of the present embodiment, a description of points that are similar to the first embodiment is omitted as appropriate.

The electronic device 100 stores estimation formulas for estimating the lipid level based on the pulse wave in the storage 145, for example, in advance. The electronic device 100 estimates the lipid level using these estimation formulas.

The estimation theory related to estimating the lipid level based on pulse wave is similar to the estimation theory for blood glucose level described in the first embodiment. In other words, a change in the lipid level of the blood is also reflected in the waveform of the pulse wave. Therefore, the electronic device 100 can acquire the pulse wave and estimate the lipid level based on the acquired pulse wave.

Figure 24:
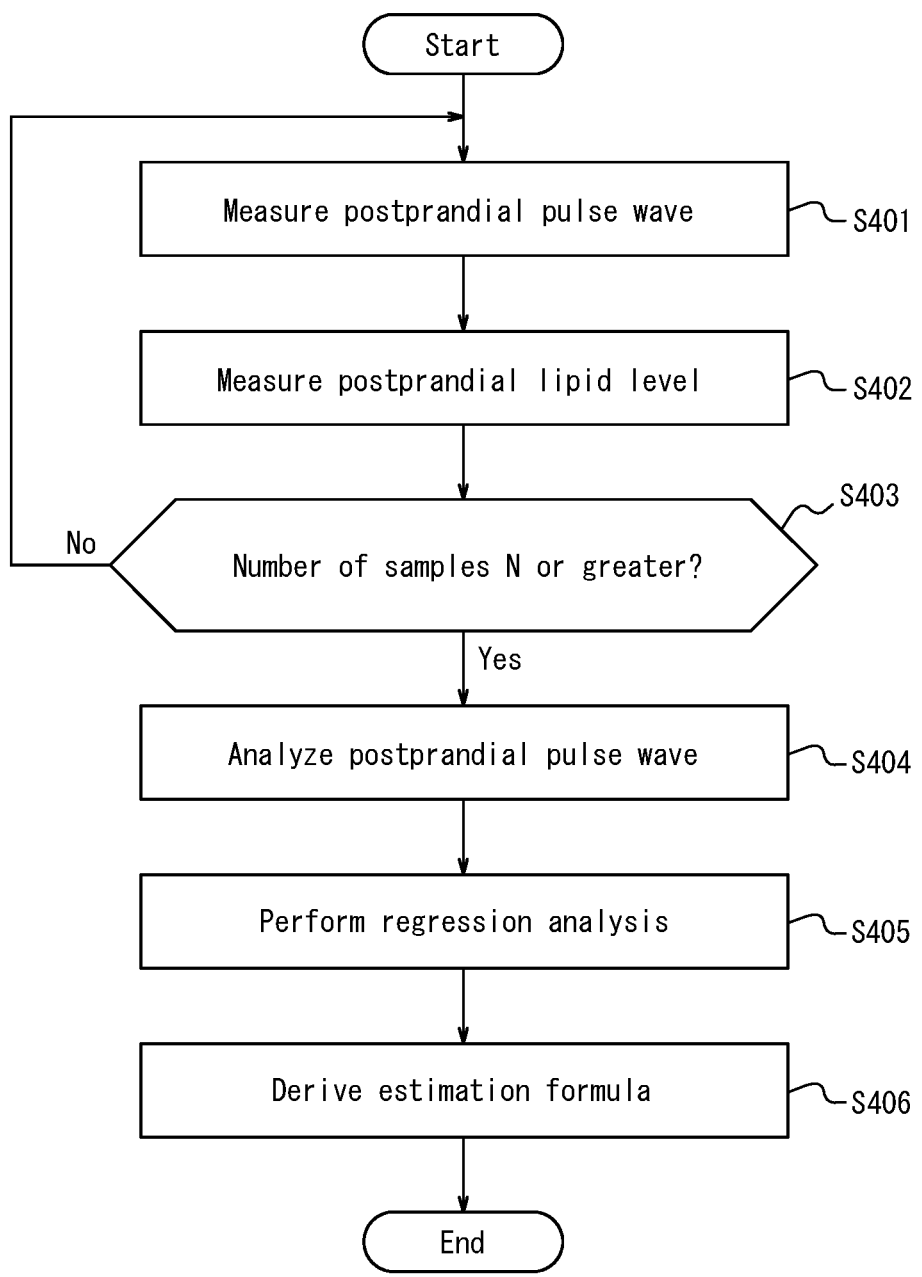
FIG. 24 is a flowchart for deriving an estimation formula used by an electronic device according to a second embodiment.

FIG. 24 is a flowchart for deriving an estimation formula used by the electronic device 100 according to the present embodiment. In the present embodiment as well, the estimation formula is derived by performing regression analysis, such as PLS regression analysis or neural network regression analysis, based on sample data. In the present embodiment, the estimation formula is derived based on the postprandial pulse wave as the sample data. "Postprandial" as used in the present embodiment may refer to a time when the lipid level is higher at a predetermined time after a meal is taken (for example, approximately three hours after the start of a meal). If the estimation formula is derived in particular by performing regression analysis using sample data for which variation in the lipid level is close to a normal distribution, the lipid level at any timing can be estimated for the subject being tested.

During derivation of the estimation formula, first, information related to the subject's postprandial pulse wave, as measured by a pulse wave meter, is inputted into the estimation formula derivation apparatus (step S401).

Information related to the subject's postprandial lipid level, as measured by a lipid measurement apparatus, is also inputted into the estimation formula derivation apparatus (step S402). The age of the subject for each set of sample data may also be inputted in steps S401 and S402.

The estimation formula derivation apparatus determines whether the number of samples in the sample data inputted in step S401 and step S402 is N or greater, which is an amount sufficient for regression analysis (step S403). The sample number N can be determined appropriately and can be 100, for example. When determining that the number of samples is less than N (No), the estimation formula derivation apparatus repeats step S401 and step S402 until the number of samples becomes N or greater. Conversely, when determining that the number of samples is N or greater (Yes), the estimation formula derivation apparatus proceeds to step S404 and calculates the estimation formula.

During calculation of the estimation formula, the estimation formula derivation apparatus analyzes the inputted postprandial pulse wave (step S404). In the present embodiment, the estimation formula derivation apparatus analyzes the rising index SI, the AI, the AIt, and the pulse rate PR of the postprandial pulse wave. The estimation formula derivation apparatus may analyze the pulse wave by performing FFT analysis.

The estimation formula derivation apparatus then performs regression analysis (step S405). The outcome variable in the regression analysis is the postprandial lipid level. The explanatory variables in the regression analysis are, for example, the age inputted in step S401 or step S402 and the rising index SI, the AI, the AIt, and the pulse rate PR of the postprandial pulse wave analyzed in step S404. When the estimation formula derivation apparatus performs FFT analysis in step S404, the explanatory variables may, for example, be Fourier coefficients calculated as the result of the FFT analysis.

The estimation formula derivation apparatus derives an estimation formula for estimating the postprandial lipid level based on the result of regression analysis (step S406).

Figure 25:
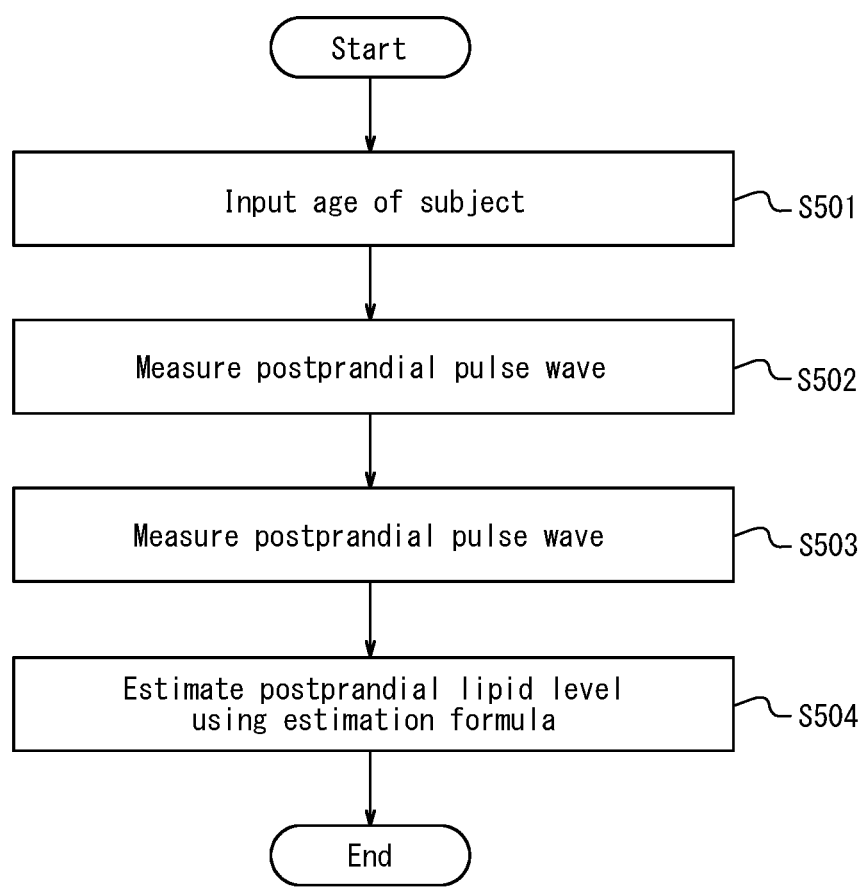
FIG. 25 is a flowchart for estimating a subject's postprandial lipid level using the estimation formula derived with the flowchart in FIG. 24.

Next, the process for estimating the subject's lipid level using an estimation formula is described. FIG. 25 is a flowchart for estimating a subject's postprandial lipid level using the estimation formula derived with the flowchart in FIG. 24, for example.

First, the electronic device 100 receives input of the subject's age in response to operation of the input interface 141 by the subject (step S501).

The electronic device 100 also measures the subject's postprandial pulse wave based on operation by the subject (step S502).

Next, the electronic device 100 analyzes the measured pulse wave (step S503). For example, the electronic device 100 analyzes the rising index SI, the AI, the AIt, and the pulse rate PR related to the measured pulse wave.

The electronic device 100 estimates the subject's postprandial lipid level by applying the rising index SI, the AI, the AIt, and the pulse rate PR analyzed in step S503 and the subject's age to the estimation formula derived with the flowchart of FIG. 24 (step S504). The subject is notified of the estimated postprandial lipid level by the notification interface 147 of the electronic device 100, for example.

In this way, the electronic device 100 according to the present embodiment uses an estimation formula derived based on the postprandial pulse wave and lipid level to estimate the subject's postprandial lipid level based on the subject's measured postprandial pulse wave. The electronic device 100 can therefore estimate the postprandial lipid level rapidly and in a non-invasive manner. Consequently, the electronic device 100 can easily estimate the subject's state of health. As an index related to pulse wave, the AIt is less affected than the AI by the reflected wave in the pulse wave. Use of the AIt, therefore, can improve the estimation accuracy of the subject's lipid level.

As described in the example of estimating the blood glucose level, the lipid level may also be estimated by selecting one estimation formula from among a plurality of estimation formulas and using the selected estimation formula to estimate the lipid level.

In the above embodiments, examples of the electronic device 100 estimating the blood glucose level and the lipid level have been described, but the blood glucose level and the lipid level are not necessarily estimated by the electronic device 100. An example of an apparatus other than the electronic device 100 estimating the blood glucose level and the lipid level is described below.

Figure 26:
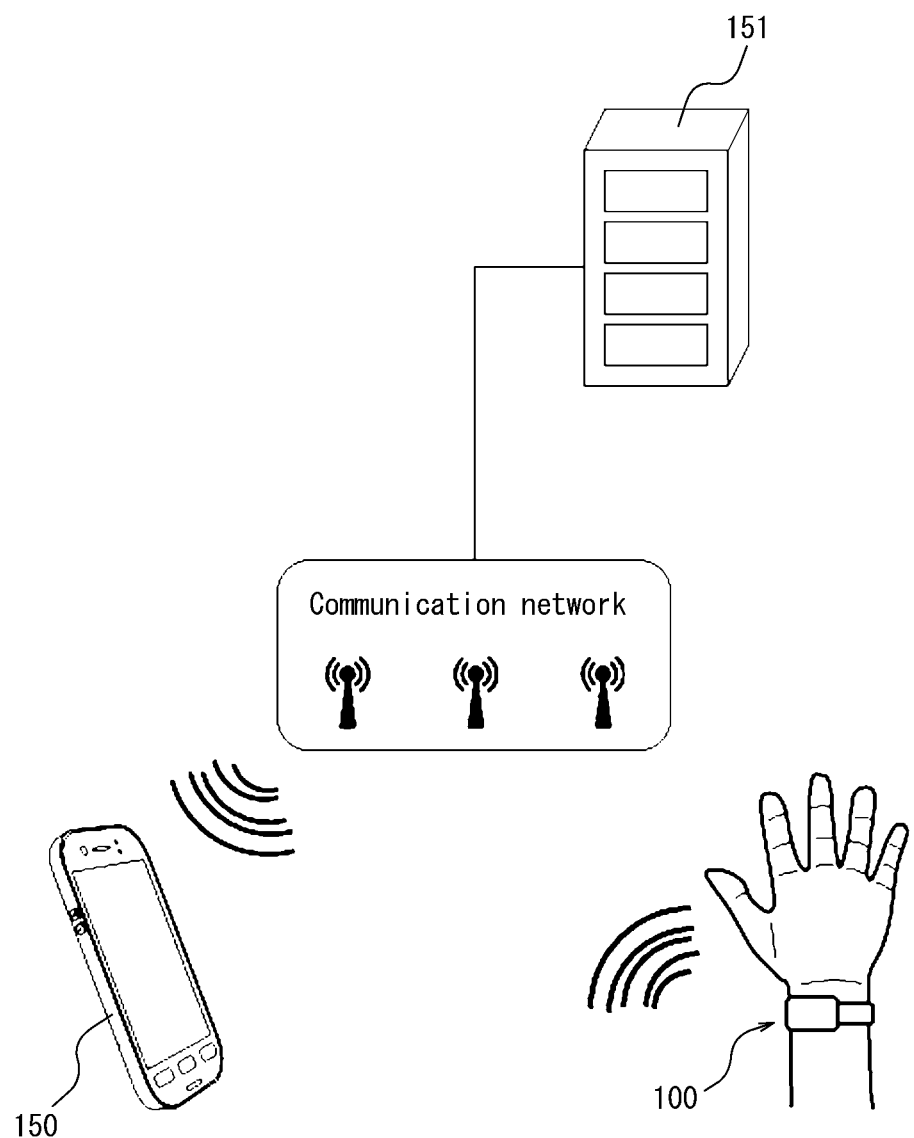
FIG. 26 schematically illustrates the configuration of a system according to an embodiment.

FIG. 26 illustrates the schematic configuration of a system according to an embodiment. The system according to the embodiment illustrated in FIG. 26 includes an electronic device 100, an information processing apparatus (such as a server) 151, a mobile terminal 150, and a communication network. As illustrated in FIG. 26, the pulse wave measured by the electronic device 100 is transmitted to the information processing apparatus 151 over a communication network and is stored on the information processing apparatus 151 as personal information of the subject. On the information processing apparatus 151, the subject's blood glucose level or lipid level is estimated by comparison with the subject's past acquired information and with a variety of databases. The information processing apparatus 151 may further prepare appropriate advice for the subject. The information processing apparatus 151 replies to the mobile terminal 150 in the subject's possession with estimation results and advice. The mobile terminal 150 can construct a system to provide notification, via the display of the mobile terminal 150, of the received estimation results and advice. Information from a plurality of users can be collected on the information processing apparatus 151 by use of the communication function of the electronic device 100, thereby further improving the estimation accuracy. Furthermore, since the mobile terminal 150 is used as notification means, the electronic device 100 does not require the notification interface 147 and can be further reduced in size. The calculation load on the controller 143 of the electronic device 100 can also be reduced, since the subject's blood glucose level or lipid level is estimated on the information processing apparatus 151. The subject's past acquired information can also be stored on the information processing apparatus 151, thereby reducing the load on the storage 145 of the electronic device 100. Therefore, the electronic device 100 can be further reduced in size and complexity. The processing speed for calculation also improves.

In the system according to the present embodiment, the electronic device 100 and the mobile terminal 150 have been illustrated as connected over the communication network via the information processing apparatus 151, but a system according to the present disclosure is not limited to this configuration. The electronic device 100 and the mobile terminal 150 may be connected directly over the communication network without use of the information processing apparatus 151.

Characteristic embodiments have been described for a complete and clear disclosure. The appended claims, however, are not limited to the above embodiments and are to be construed as encompassing all of the possible modifications and alternate configurations that a person of ordinary skill in the art could make within the scope of the fundamental features indicated in the present disclosure.

For example, in the above embodiments, the sensor 130 has been described as being provided with the angular velocity sensor 131, but the electronic device 100 according to the present disclosure is not limited to this case. The sensor 130 may be provided with an optical pulse wave sensor constituted by an optical emitter and an optical detector or may be provided with a pressure sensor. Furthermore, the electronic device 100 is not limited to being worn on the wrist. It suffices for the sensor 130 to be placed on an artery, such as on the neck, ankle, thigh, ear, or the like.

For example, in the above embodiments, the explanatory variables in the regression analysis, such as PLS regression analysis or neural network regression analysis, have been described as being age, rising index SI, AI, AIt, and pulse rate PR. The explanatory variables need not, however, include all five of these.

For example, the explanatory variables of regression analysis, such as PLS regression analysis or neural network regression analysis, need not include an index determined based on the acceleration pulse wave. The index determined based on the acceleration pulse wave is, for example, the rising index SI. For example, when the effect of the reflected wave on the pulse wave is large, as described with reference to FIGS. 15 and 16, the effect of the reflected wave is also evident in the acceleration pulse wave. The estimation accuracy of the subject's blood glucose level or lipid level may worsen when the effect of the reflected wave is evident in the acceleration pulse wave in this way. An index determined based on the acceleration pulse wave need not be used as an explanatory variable in such a case. When the acceleration pulse wave b/a is not used as an explanatory variable in PLS regression analysis or neural network regression analysis, then age, pulse rate, AI, AIt, and the like can be appropriately selected as explanatory variables.

Figure 27:
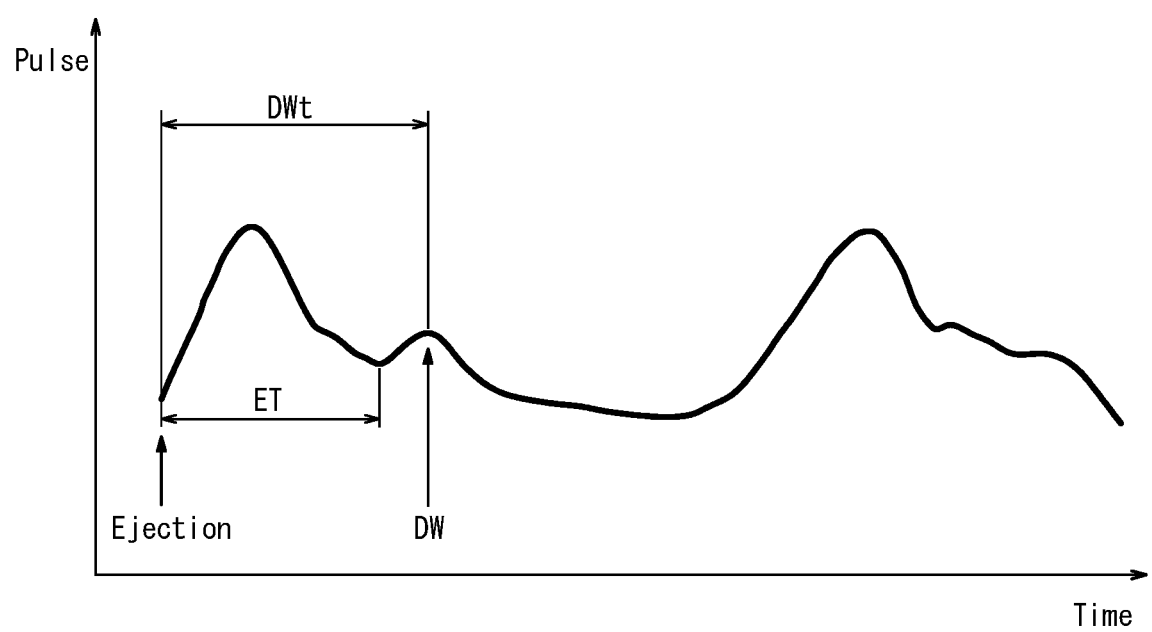
FIG. 27 illustrates an example pulse wave.

The explanatory variables may include variables other than these five variables. For example, the explanatory variables may include sex, an index determined based on the velocity pulse wave yielded by the first derivative of the pulse wave, or the like. The explanatory variables may, for example, include an index determined based on pulse. The index based on pulse may, for example, include the ejection time (ET) or the time DWt from heart chamber ejection until a dicrotic wave (DW), examples of which are illustrated in FIG. 27. The explanatory variables may, for example, include the fasting blood glucose level (such as the blood glucose level measured by blood sampling or the blood glucose level measured in advance during a physical examination).

The estimation formula has been described in the above embodiments as being derived based on the postprandial pulse wave and the blood glucose level or lipid level. The estimation formula is not, however, necessarily derived based on the postprandial pulse wave and the blood glucose level or lipid level. The estimation formula may, for example, be derived from an appropriate combination of the preprandial and postprandial pulse waves and the preprandial and postprandial blood glucose level or lipid level.

The invention claimed is:

1. An electronic device comprising:
a sensor configured to acquire a pulse wave of a subject; and
a controller configured to analyze, based on the pulse wave of the subject acquired by the sensor, a rate of change in the pulse wave at a predetermined time after a point in time exhibiting a peak of the pulse wave and to estimate a blood glucose level of the subject based on the rate of change, the predetermined time being a fixed value.

2. The electronic device of claim 1, wherein the predetermined time is substantially 100 msec.

3. The electronic device of claim 1, wherein the controller is configured to estimate the blood glucose level of the subject by applying the rate of change to an estimation formula.

4. The electronic device of claim 3, wherein the estimation formula is derived based on a postprandial pulse wave and a postprandial blood glucose level.

5. The electronic device of claim 3, wherein the controller is configured to estimate the blood glucose level of the subject by using the estimation formula the estimation formula being selected from a plurality of estimation formulas based on a content of a meal.

6. The electronic device of claim 5, wherein each estimation formula among the plurality of estimation formulas corresponds to a category of the content of the meal.

7. The electronic device of claim 3, wherein the estimation formula is derived by PLS regression analysis or neural network regression analysis.

8. The electronic device of claim 3, wherein the controller is configured to further apply an index based on a velocity of the pulse wave to the estimation formula when estimating the blood glucose level of the subject.

9. An electronic device comprising:
a sensor configured to acquire a pulse wave of a subject; and
a controller configured to analyze, based on the pulse wave of the subject acquired by the sensor, a rate of change in the pulse wave at a predetermined time after a point in time exhibiting a peak of the pulse wave and to estimate a lipid level of the subject based on the rate of change, the predetermined time being a fixed value.

10. An estimation system comprising an electronic device and an information processing apparatus connected communicably with each other,
wherein the electronic device comprises a sensor configured to acquire a pulse wave of a subject; and
the information processing apparatus comprises a controller configured to analyze, based on the pulse wave of the subject acquired by the sensor, a rate of change in the pulse wave at a predetermined time after a point in time exhibiting a peak of the pulse wave and to estimate a blood glucose level of the subject based on the rate of change, the predetermined time being a fixed value.

11. An estimation system comprising an electronic device and
an information processing apparatus connected communicably with each other, wherein the electronic device comprises a sensor configured to acquire a pulse wave of a subject; and
the information processing apparatus comprises a controller configured to analyze, based on the pulse wave of the subject acquired by the sensor, a rate of change in the pulse wave at a predetermined time after a point in time exhibiting a peak of the pulse wave and to estimate a lipid level of the subject based on the rate of change, the predetermined time being a fixed value.

12. An estimation method to be executed by an electronic device, the estimation method comprising:
acquiring a pulse wave of a subject;
analyzing, based on the pulse wave of the subject, a rate of change in the pulse wave at a predetermined time after a point in time exhibiting a peak of the pulse wave, the predetermined time being a fixed value; and
estimating a blood glucose level of the subject based on the rate of change.

13. An estimation method to be executed by an electronic device, the estimation method comprising:
acquiring a pulse wave of a subject;
analyzing, based on the pulse wave of the subject, a rate of change in the pulse wave at a predetermined time after a point in time exhibiting a peak of the pulse wave, the predetermined time being a fixed value; and
estimating a lipid level of the subject based on the rate of change.

14. A non-transitory computer readable storage medium which stores an estimation program for causing an electronic device to execute the steps of:
acquiring a pulse wave of a subject;
analyzing, based on the pulse wave of the subject, a rate of change in the pulse wave at a predetermined time after a point in time exhibiting a peak of the pulse wave, the predetermined time being a fixed value; and
estimating a blood glucose level of the subject based on the rate of change.

15. A non-transitory computer readable storage medium which stores an estimation program for causing an electronic device to execute the steps of:
acquiring a pulse wave of a subject;
analyzing, based on the pulse wave of the subject, a rate of change in the pulse wave at a predetermined time after a point in time exhibiting a peak of the pulse wave, the predetermined time being a fixed value; and
estimating a lipid level of the subject based on the rate of change.

* * * * *